(12) United States Patent
Lewis et al.

(10) Patent No.: US 11,331,351 B2
(45) Date of Patent: *May 17, 2022

(54) BACILLUS STRAINS IMPROVING HEALTH AND PERFORMANCE OF PRODUCTION ANIMALS

(71) Applicants: Novozymes A/S, Bagsvaerd (DK); Adisseo France SAS, Antony (FR)

(72) Inventors: Derrick Lewis, Durham, NC (US); Marianne Thorup Cohn, Copenhagen (DK); Adam Nelson, Salem, VA (US); Preben Nielsen, Horsholm (DK); Estelle Devillard, Antony (FR); Lamya Rhayat, Antony (FR)

(73) Assignees: Novozymes A/S, Bagsvaerd (DK); Adisseo France SAS, Antony (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/543,663

(22) PCT Filed: Jan. 22, 2016

(86) PCT No.: PCT/US2016/014492
§ 371 (c)(1),
(2) Date: Jul. 14, 2017

(87) PCT Pub. No.: WO2016/118840
PCT Pub. Date: Jul. 28, 2016

(65) Prior Publication Data
US 2018/0264052 A1 Sep. 20, 2018

Related U.S. Application Data

(60) Provisional application No. 62/109,210, filed on Jan. 29, 2015, provisional application No. 62/106,869, filed on Jan. 23, 2015, provisional application No. 62/260,892, filed on Nov. 30, 2015.

(51) Int. Cl.
| | | |
|---|---|---|
| *A61K 35/742* | (2015.01) | |
| *A23K 10/18* | (2016.01) | |
| *A23K 50/75* | (2016.01) | |
| *A23K 50/30* | (2016.01) | |
| *C12N 1/20* | (2006.01) | |
| *A61P 31/04* | (2006.01) | |
| *A61P 31/00* | (2006.01) | |
| *A61P 3/00* | (2006.01) | |
| *C12R 1/07* | (2006.01) | |
| *C12R 1/125* | (2006.01) | |

(52) U.S. Cl.
CPC .......... *A61K 35/742* (2013.01); *A23K 10/18* (2016.05); *A23K 50/30* (2016.05); *A23K 50/75* (2016.05); *A61P 3/00* (2018.01); *A61P 31/04* (2018.01); *C12N 1/205* (2021.05); *A61P 31/00* (2018.01); *C12R 2001/07* (2021.05); *C12R 2001/125* (2021.05)

(58) Field of Classification Search
None
See application file for complete search history.

(56) References Cited

U.S. PATENT DOCUMENTS

| | | | |
|---|---|---|---|
| 4,919,936 A | 4/1990 | Iwanami | |
| 5,733,355 A * | 3/1998 | Hibino | A01K 1/0152 435/262 |
| 8,540,981 B1 | 9/2013 | Wehnes | |
| 8,906,668 B2 * | 12/2014 | Henn | A61K 38/13 435/252.4 |
| 2004/0101525 A1 | 5/2004 | Lin | |
| 2009/0280090 A1 | 11/2009 | Rehberger | |
| 2009/0318292 A1 | 12/2009 | Kong | |
| 2011/0318289 A1 | 12/2011 | Frodyma | |
| 2013/0136695 A1 | 5/2013 | Hargis | |
| 2013/0330307 A1 | 12/2013 | Millan | |
| 2014/0037582 A1 | 2/2014 | Romero | |
| 2014/0234279 A1 | 8/2014 | Millan | |

FOREIGN PATENT DOCUMENTS

| | | |
|---|---|---|
| CN | 103882097 | 6/2014 |
| WO | 2007/064741 A2 | 6/2007 |
| WO | 2010/033714 A1 | 3/2010 |
| WO | 2012/009712 A2 | 1/2012 |
| WO | 2012/105805 A2 | 9/2012 |
| WO | 2013/029013 A1 | 2/2013 |
| WO | 2013/096369 A1 | 6/2013 |
| WO | 2013/153159 A1 | 10/2013 |
| WO | 2014/169046 A1 | 10/2014 |

OTHER PUBLICATIONS

Paineau et al. FEMS Immunol Med Microbiol 53( 2008):107-113.*
Anonymous, EFSA Journal, vol. 8, No. 3, article 1552, pp. 1-7 (2010).
Anonymous, EFSA Journal, vol. 10, No. 1, article 2536, pp. 1-19 (2012).
Anonymous, EFSA Supporting Publication, article EN-587, pp. 1-13 (2014).
Essghaier et al., Journal of Applied Microbiology, vol. 106, No. 3, pp. 833-846 (2009).
Gang et al., Biomed. Environ. Sci., vol. 28, No. 8, pp. 620-625 (2015).
Jayaraman et al., Poultry Science, vol. 92, No. 2, pp. 370-374 (2013).
Knap et al., Avian Diseases, vol. 54, No. 2, pp. 931-935 (2010).
Maruta et al., Anim. Sci. Technol. (Jpn.), vol. 67, No. 5, pp. 403-409 (1996).

(Continued)

*Primary Examiner* — Oluwatosin A Ogunbiyi
(74) *Attorney, Agent, or Firm* — Adam Rucker

(57) ABSTRACT

The present invention relates to animal feed or animal feed additive comprising *Bacillus* strains which improve the health and performance of production animals. The invention further relates use of the *Bacillus* strains in animal feed and animal feed additives.

12 Claims, 3 Drawing Sheets
Specification includes a Sequence Listing.

(56) References Cited

OTHER PUBLICATIONS

Prieto et al., Marine Drugs, vol. 12, No. 5, pp. 2422-2445 (2014).
Sathishkumar et al., Kemin Animal Nutrition and Health, "Influence of CLOSTAT on Production Performance of Commercial Layers (BV 300)" (2013).
Tactacan et al., J. Appl. Poult. Res., vol. 22, No. 4, pp. 825-831 (2013).
Teo et al., J. Appl. Poult. Res., vol. 15, No. 2, pp. 229-235 (2006).
Zeigler, UniProtKB Accession No. E0TXL5 (2010).

* cited by examiner

```
                          250        260        270        280        290        300        310        320
                          |          |          |          |          |          |          |          |
AJ276351 B subtilis       AACGGCTCACCAAGGCAACGATGCGTAGCCGACCTGAGAGGGTGATCGGCCACACTGAGACACTGGGACTGAGACACGGCCCAGACTC 320
DSM29871                  AACGGCTCACCAAGGCAACGATGCGTAGCCGACCTGAGAGGGTGATCGGCCACACTGAGACACTGGGACTGAGACACGGCCCAGACTC 320
DSM29870                  AACGGCTCACCAAGGCAACGATGCGTAGCCGACCTGAGAGGGTGATCGGCCACACTGAGACACTGGGACTGAGACACGGCCCAGACTC 320
AB021198 B vallismortis   AA[T]GCTCACCAAGGCAACGATGCGTAGCCGACCTGAGAGGGTGATCGGCCACACTGAGACACTGGGACTGAGACACGGCCCAGACTC 320
AB255669 B amyloliquefaciens AACGGCTCACCAAGG[C]ACGATGCGTAGCCGACCTGAGAGGGTGATCGGCCACACTGAGACACTGGGACTGAGACACGGCCCAGACTC 320
DSM29869                  AACGGCTCACCAAGGCAACGATGCGTAGCCGACCTGAGAGGGTGATCGGCCACACTGAGACACTGGGACTGAGACACGGCCCAGACTC 320
DSM29872                  AACGGCTCACCAAGG[C]ACGATGCGTAGCCGACCTGAGAGGGTGATCGGCCACACTGAGACACTGGGACTGAGACACGGCCCAGACTC 320

330        340        350        360        370        380        390        400
                          |          |          |          |          |          |          |          |
AJ276351 B subtilis       CTACGGGAGGCAGCAGTAGGGAATCTTCCGCAATGGACGAAAGTCTGACGGAGCAACGCCGCGTGAGTGATGAAGGTTTT 400
DSM29871                  CTACGGGAGGCAGCAGTAGGGAATCTTCCGCAATGGACGAAAGTCTGACGGAGCAACGCCGCGTGAGTGATGAAGGTTTT 400
DSM29870                  CTACGGGAGGCAGCAGTAGGGAATCTTCCGCAATGGACGAAAGTCTGACGGAGCAACGCCGCGTGAGTGATGAAGGTTTT 400
AB021198 B vallismortis   CTACGGGAGGCAGCAGTAGGGAATCTTCCGCAATGGACGAAAGTCTGACGGAGCAACGCCGCGTGAGTGATGAAGGTTTT 400
AB255669 B amyloliquefaciens CTACGGGAGGCAGCAGTAGGGAATCTTCCGCAATGGACGAAAGTCTGACGGAGCAACGCCGCGTGAGTGATGAAGGTTTT 400
DSM29869                  CTACGGGAGGCAGCAGTAGGGAATCTTCCGCAATGGACGAAAGTCTGACGGAGCAACGCCGCGTGAGTGATGAAGGTTTT 400
DSM29872                  CTACGGGAGGCAGCAGTAGGGAATCTTCCGCAATGGACGAAAGTCTGACGGAGCAACGCCGCGTGAGTGATGAAGGTTTT 400

410        420        430        440        450        460        470        480
                          |          |          |          |          |          |          |          |
AJ276351 B subtilis       CGGATCGTAAAGCTCTGTTGTTAGGGAAGAACAAGT[A]CCGTTC[G]AATAGGGCGG[T]ACCTTGACGGTACCTAACCAGAAAG 480
DSM29871                  CGGATCGTAAAGCTCTGTTGTTAGGGAAGAACAAGT[A]CCGTTC[G]AATAGGGCGG[T]ACCTTGACGGTACCTAACCAGAAAG 480
DSM29870                  CGGATCGTAAAGCTCTGTTGTTAGGGAAGAACAAGT[A]CCGTTC[G]AATAGGGCGG[T]ACCTTGACGGTACCTAACCAGAAAG 480
AB021198 B vallismortis   CGGATCGTAAAGCTCTGTTGTTAGGGAAGAACAAGTACCGTTCGAATAGGGCGGCACCTTGACGGTACCTAACCAGAAAG 480
AB255669 B amyloliquefaciens CGGATCGTAAAGCTCTGTTGTTAGGGAAGAACAAGTGCCGTTCAAATAGGGCGGCACCTTGACGGTACCTAACCAGAAAG 480
DSM29869                  CGGATCGTAAAGCTCTGTTGTTAGGGAAGAACAAGTGCCGTTCAAATAGGGCGGCACCTTGACGGTACCTAACCAGAAAG 480
DSM29872                  CGGATCGTAAAGCTCTGTTGTTAGGGAAGAACAAGTGCCGTTCAAATAGGGCGGCACCTTGACGGTACCTAACCAGAAAG 480
```

FIG. 1B

|  | 1210 | 1220 | 1230 | 1240 | 1250 | 1260 | 1270 | 1280 |  |
|---|---|---|---|---|---|---|---|---|---|
| AJ276351 B subtilis | GGCTACACACGTGCTACAATGGACAGAACAAAGGGCAGCCAACTCGCGAGAGTGCGAAACCGCGAGGTTAAGCCAATCCCACAAATCTGTTCTCAG | | | | | | | | 1280 |
| DSM29871 | GGCTACACACGTGCTACAATGGACAGAACAAAGGGCAGCCAACTCGCGAGAGTGCGAAACCGCGAGGTTAAGCCAATCCCACAAATCTGTTCTCAG | | | | | | | | 1280 |
| DSM29870 | GGCTACACACGTGCTACAATGGACAGAACAAAGGGCAGCCAACTCGCGAGAGTGCGAAACCGCGAGGTTAAGCCAATCCCACAAATCTGTTCTCAG | | | | | | | | 1280 |
| AB021198 B vallismortis | GGCTACACACGTGCTACAATGGACAGAACAAAGGGCAGCCAACTCGCGAGAGTGCGAAACCGCGAGGTTAAGCCAATCCCACAAATCTGTTCTCAG | | | | | | | | 1280 |
| AB255669 B amyloliquefaciens | GGCTACACACGTGCTACAATGG[CG]CAGAACAAAGGGCAGCCAACTCGCGAAACCGCGAGGTTAAGCCAATCCCACAAATCTGTTCTCAG | | | | | | | | 1280 |
| DSM29869 | GGCTACACACGTGCTACAATGG[CG]CAGAACAAAGGGCAGCCAACTCGCGAAACCGCGAGGTTAAGCCAATCCCACAAATCTGTTCTCAG | | | | | | | | 1280 |
| DSM29872 | GGCTACACACGTGCTACAATGGACAGAACAAAGGGCAGCCAACTCGCGAGAGTGCGAAACCGCGAGGTTAAGCCAATCCCACAAATCTGTTCTCAG | | | | | | | | 1280 |

|  | 1290 | 1300 | 1310 | 1320 | 1330 | 1340 | 1350 | 1360 |  |
|---|---|---|---|---|---|---|---|---|---|
| AJ276351 B subtilis | TTCGGATCGCAGTCTGCAACTCGACTGCGTGAAGCTGGAATCGCTAGTAATCGCGGATCAGCATGCCGCGGTGAATACGT | | | | | | | | 1360 |
| DSM29871 | TTCGGATCGCAGTCTGCAACTCGACTGCGTGAAGCTGGAATCGCTAGTAATCGCGGATCAGCATGCCGCGGTGAATACGT | | | | | | | | 1360 |
| DSM29870 | TTCGGATCGCAGTCTGCAACTCGACTGCGTGAAGCTGGAATCGCTAGTAATCGCGGATCAGCATGCCGCGGTGAATACGT | | | | | | | | 1360 |
| AB021198 B vallismortis | TTCGGATCGCAGTCTGCAACTCGACTGCGTGAAGCTGGAATCGCTAGTAATCGCGGATCAGCATGCCGCGGTGAATACGT | | | | | | | | 1360 |
| AB255669 B amyloliquefaciens | TTCGGATCGCAGTCTGCAACTCGACTGCGTGAAGCTGGAATCGCTAGTAATCGCGGATCAGCATGCCGCGGTGAATACGT | | | | | | | | 1360 |
| DSM29869 | TTCGGATCGCAGTCTGCAACTCGACTGCGTGAAGCTGGAATCGCTAGTAATCGCGGATCAGCATGCCGCGGTGAATACGT | | | | | | | | 1360 |
| DSM29872 | TTCGGATCGCAGTCTGCAACTCGACTGCGTGAAGCTGGAATCGCTAGTAATCGCGGATCAGCATGCCGCGGTGAATACGT | | | | | | | | 1360 |

|  | 1370 | 1380 | 1390 | 1400 | 1410 | 1420 | 1430 | 1440 |  |
|---|---|---|---|---|---|---|---|---|---|
| AJ276351 B subtilis | TCCCGGGCCTTGTACACACCGCCCGTCACACCACGAGAGTTTGTAACACCCGAAGTCGGTGAGGTAACCTTTTAGGAGCC | | | | | | | | 1440 |
| DSM29871 | TCCCGGGCCTTGTACACACCGCCCGTCACACCACGAGAGTTTGTAACACCCGAAGTCGGTGAGGTAACCTTTTAGGAGCC | | | | | | | | 1440 |
| DSM29870 | TCCCGGGCCTTGTACACACCGCCCGTCACACCACGAGAGTTTGTAACACCCGAAGTCGGTGAGGTAACCTTTTAGGAGCC | | | | | | | | 1440 |
| AB021198 B vallismortis | TCCCGGGCCTTGTACACACCGCCCGTCACACCACGAGAGTTTGTAACACCCGAAGTCGGTGAGGTAACCTTTTAGGAGCC | | | | | | | | 1440 |
| AB255669 B amyloliquefaciens | TCCCGGGCCTTGTACACACCGCCCGTCACACCACGAGAGTTTGTAACACCCGAAGTCGGTGAGGTAACCTTTTAGGAGCC | | | | | | | | 1440 |
| DSM29869 | TCCCGGGCCTTGTACACACCGCCCGTCACACCACGAGAGTTTGTAACACCCGAAGTCGGTGAGGTAACCTTTT[T]GGAGCC | | | | | | | | 1440 |
| DSM29872 | TCCCGGGCCTTGTACACACCGCCCGTCACACCACGAGAGTTTGTAACACCCGAAGTCGGTGAGGTAACCTTT[A]AGGAGCC | | | | | | | | 1440 |

FIG. 1C

SEQUENCE LISTING

<160> NUMBER OF SEQ ID NOS: 13

<210> SEQ ID NO 1
<211> LENGTH: 1507
<212> TYPE: DNA
<213> ORGANISM: Bacillus amyloliquefaciens

<400> SEQUENCE: 1

```
gacgaacgct ggcggcgtgc ctaatacatg caagtcgagc ggacagatgg gagcttgctc      60
cctgatgtta gcggcggacg ggtgagtaac acgtgggtaa cctgcctgta agactgggat     120
aactccggga aaccggggct aataccggat ggttgtttga accgcatggt tcagacataa     180
aaggtggctt cggctaccac ttacagatgg acccgcggcg cattagctag ttggtgaggt     240
aacggctcac caaggcaacg atgcgtagcc gacctgagag ggtgatcggc cacactggga     300
ctgagacacg gcccagactc ctacgggagg cagcagtagg gaatcttccg caatggacga     360
aagtctgacg gagcaacgcc gcgtgagtga tgaaggtttt cggatcgtaa agctctgttg     420
ttagggaaga acaagtgccg ttcaaatagg gcggcacctt gacggtacct aaccagaaag     480
ccacggctaa ctacgtgcca gcagccgcgg taatacgtag gtggcaagcg ttgtccggaa     540
ttattgggcg taaagggctc gcaggcggtt tcttaagtct gatgtgaaag cccccggctc     600
aaccggggag ggtcattgga aactgggaa cttgagtgca gaagaggaga gtggaattcc      660
acgtgtagcg gtgaaatgcg tagagatgtg gaggaacacc agtggcgaag gcgactctct     720
ggtctgtaac tgacgctgag gagcgaaagc gtggggagcg aacaggatta gataccctgg     780
tagtccacgc cgtaaacgat gagtgctaag tgttaggggg tttccgcccc ttagtgctgc     840
agctaacgca ttaagcactc cgcctgggga gtacggtcgc aagactgaaa ctcaaaggaa     900
ttgacggggg cccgcacaag cggtggagca tgtggtttaa ttcgaagcaa cgcgaagaac     960
cttaccaggt cttgacatcc tctgacaatc ctagagatag gacgtcccct tcggggcag    1020 agtgacaggt ggtgcatggt tgtcgtcagc tcgtgtcgtg agatgttggg ttaagtcccg    1080
caacgagcgc aaccccttgat cttagttgcc agcattcagt tgggcactct aaggtgactg    1140
ccggtgacaa accggaggaa ggtggggatg acgtcaaatc atcatgcccc ttatgacctg    1200
ggctacacac gtgctacaat gggcagaaca aagggcagcg aaaccgcgag gttaagccaa    1260
tcccacaaat ctgttctcag ttcggatcgc agtctgcaac tcgactgcgt gaagctggaa    1320
tcgctagtaa tcgcggatca gcatgccgcg gtgaatacgt tcccgggcct tgtacacacc    1380
```

| gcccgtcaca ccacgagagt ttgtaacacc cgaagtcggt gaggtaacct tttaggagcc | 1440 |
| agccgccgaa ggtgggacag atgattgggg tgaagtcgta acaaggtagc cgtatcggaa | 1500 |
| ggtgcgg | 1507 |

<210> SEQ ID NO 2
<211> LENGTH: 1507
<212> TYPE: DNA
<213> ORGANISM: Bacillus subtilis

<400> SEQUENCE: 2

| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactgggat | 120 |
| aactccggga aaccggggct aataccggat gcttgtttga accgcatggt tcaaacataa | 180 |
| aaggtggctt cggctaccac ttacagatgg acccgcggcg cattagctag ttggtgaggt | 240 |
| aacggctcac caaggcaacg atgcgtagcc gacctgagag ggtgatcggc cacactggga | 300 |
| ctgagacacg gcccagactc ctacgggagg cagcagtagg gaatcttccg caatggacga | 360 |
| aagtctgacg gagcaacgcc gcgtgagtga tgaaggtttt cggatcgtaa agctctgttg | 420 |
| ttagggaaga acaagtaccg ttcgaatagg gcggtacctt gacggtacct aaccagaaag | 480 |
| ccacggctaa ctacgtgcca gcagccgcgg taatacgtag gtggcaagcg ttgtccggaa | 540 |
| ttattgggcg taagggctc gcaggcggtt tcttaagtct gatgtgaaag cccccggctc | 600 |
| aaccggggag ggtcattgga aactgggaa cttgagtgca gaagaggaga gtggaattcc | 660 |
| acgtgtagcg gtgaaatgcg tagagatgtg gaggaacacc agtggcgaag gcgactctct | 720 |
| ggtctgtaac tgacgctgag gagcgaaagc gtggggagcg aacaggatta gataccctgg | 780 |
| tagtccacgc cgtaaacgat gagtgctaag tgttaggggg tttccgcccc ttagtgctgc | 840 |
| agctaacgca ttaagcactc cgcctgggga gtacggtcgc aagactgaaa ctcaaaggaa | 900 |
| ttgacggggg cccgcacaag cggtggagca tgtggtttaa ttcgaagcaa cgcgaagaac | 960 |
| cttaccaggt cttgacatcc tctgacaatc ctagagatag gacgtcccct tcggggcag | 1020 |
| agtgacaggt ggtgcatggt tgtcgtcagc tcgtgtcgtg agatgttggg ttaagtcccg | 1080 |
| caacgagcgc aacccttgat cttagttgcc agcattcagt tgggcactct aaggtgactg | 1140 |
| ccggtgacaa accggaggaa ggtggggatg acgtcaaatc atcatgcccc ttatgacctg | 1200 |
| ggctacacac gtgctacaat ggacagaaca aagggcagcg aaaccgcgag gttaagccaa | 1260 |
| tcccacaaat ctgttctcag ttcggatcgc agtctgcaac tcgactgcgt gaagctggaa | 1320 |
| tcgctagtaa tcgcggatca gcatgccgcg gtgaatacgt tcccgggcct tgtacacacc | 1380 |
| gcccgtcaca ccacgagagt ttgtaacacc cgaagtcggt gaggtaacct tttaggagcc | 1440 |
| agccgccgaa ggtgggacag atgattgggg tgaagtcgta acaaggtagc cgtatcggaa | 1500 |
| ggtgcgg | 1507 |

<210> SEQ ID NO 3
<211> LENGTH: 1507
<212> TYPE: DNA
<213> ORGANISM: Bacillus subtilis

<400> SEQUENCE: 3

| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactgggat | 120 |

| | |
|---|---|
| aactccggga aaccggggct aataccggat ggttgtttga accgcatggt tcaaacataa | 180 |
| aaggtggctt cggctaccac ttacagatgg acccgcggcg cattagctag ttggtgaggt | 240 |
| aacggctcac caaggcaacg atgcgtagcc gacctgagag ggtgatcggc cacactggga | 300 |
| ctgagacacg gcccagactc ctacgggagg cagcagtagg gaatcttccg caatggacga | 360 |
| aagtctgacg gagcaacgcc gcgtgagtga tgaaggtttt cggatcgtaa agctctgttg | 420 |
| ttagggaaga caagtaccg ttcgaatagg gcggtacctt gacggtacct aaccagaaag | 480 |
| ccacggctaa ctacgtgcca gcagccgcgg taatacgtag gtggcaagcg ttgtccggaa | 540 |
| ttattgggcg taaagggctc gcaggcggtt tcttaagtct gatgtgaaag ccccggctc | 600 |
| aaccggggag ggtcattgga aactgggaa cttgagtgca gaagaggaga gtggaattcc | 660 |
| acgtgtagcg gtgaaatgcg tagagatgtg gaggaacacc agtggcgaag gcgactctct | 720 |
| ggtctgtaac tgacgctgag gagcgaaagc gtggggagcg aacaggatta gatacctgg | 780 |
| tagtccacgc cgtaaacgat gagtgctaag tgttagggg tttccgcccc ttagtgctgc | 840 |
| agctaacgca ttaagcactc cgcctgggga gtacggtcgc aagactgaaa ctcaaaggaa | 900 |
| ttgacggggg cccgcacaag cggtggagca tgtggtttaa ttcgaagcaa cgcgaagaac | 960 |
| cttaccaggt cttgacatcc tctgacaatc ctagagatag gacgtcccct tcggggcag | 1020 |
| agtgacaggt ggtgcatggt tgtcgtcagc tcgtgtcgtg agatgttggg ttaagtcccg | 1080 |
| caacgagcgc aacccttgat cttagttgcc agcattcagt tgggcactct aaggtgactg | 1140 |
| ccggtgacaa accggaggaa ggtggggatg acgtcaaatc atcatgcccc ttatgacctg | 1200 |
| ggctacacac gtgctacaat ggacagaaca aagggcagcg aaaccgcgag gttaagccaa | 1260 |
| tcccacaaat ctgttctcag ttcggatcgc agtctgcaac tcgactgcgt gaagctggaa | 1320 |
| tcgctagtaa tcgcggatca gcatgccgcg gtgaatacgt tcccgggcct tgtacacacc | 1380 |
| gcccgtcaca ccacgagagt ttgtaacacc cgaagtcggt gaggtaacct tttaggagcc | 1440 |
| agccgccgaa ggtgggacag atgattgggg tgaagtcgta acaaggtagc cgtatcggaa | 1500 |
| ggtgcgg | 1507 |

```
<210> SEQ ID NO 4
<211> LENGTH: 1507
<212> TYPE: DNA
<213> ORGANISM: Bacillus amyloliquefaciens

<400> SEQUENCE: 4
```

| | |
|---|---|
| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactgggat | 120 |
| aactccggga aaccggggct aataccggat ggttgtctga accgcatggt tcagacataa | 180 |
| aaggtggctt cggctaccac ttacagatgg acccgcggcg cattagctag ttggtgaggt | 240 |
| aacggctcac caaggcgacg atgcgtagcc gacctgagag ggtgatcggc cacactggga | 300 |
| ctgagacacg gcccagactc ctacgggagg cagcagtagg gaatcttccg caatggacga | 360 |
| aagtctgacg gagcaacgcc gcgtgagtga tgaaggtttt cggatcgtaa agctctgttg | 420 |
| ttagggaaga caagtgccg ttcaaatagg gcggcacctt gacggtacct aaccagaaag | 480 |
| ccacggctaa ctacgtgcca gcagccgcgg taatacgtag gtggcaagcg ttgtccggaa | 540 |
| ttattgggcg taaagggctc gcaggcggtt tcttaagtct gatgtgaaag ccccggctc | 600 |
| aaccggggag ggtcattgga aactgggaa cttgagtgca gaagaggaga gtggaattcc | 660 |
| acgtgtagcg gtgaaatgcg tagagatgtg gaggaacacc agtggcgaag gcgactctct | 720 |

```
ggtctgtaac tgacgctgag gagcgaaagc gtggggagcg aacaggatta gatacccctgg    780 tagtccacgc cgtaaacgat gagtgctaag tgttagggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct cggggggcag   1020
agtgacaggt ggtgcatggt tgtcgtcagc tcgtgtcgtg agatgttggg ttaagtcccg   1080
caacgagcgc aaccccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat ggacagaaca agggcagcg aaaccgcgag gttaagccaa   1260
tcccacaaat ctgttctcag ttcggatcgc agtctgcaac tcgactgcgt gaagctggaa   1320
tcgctagtaa tcgcggatca gcatgccgcg gtgaatacgt tcccgggcct tgtacacacc   1380
gcccgtcaca ccacgagagt ttgtaacacc cgaagtcggt gaggtaacct ttaaggagcc   1440
agccgccgaa ggtgggacag atgattgggg tgaagtcgta acaaggtagc cgtatcggaa   1500
ggtgcgg                                                              1507

<210> SEQ ID NO 5
<211> LENGTH: 1472
<212> TYPE: DNA
<213> ORGANISM: Bacillus vallismortis

<400> SEQUENCE: 5
gacgaacgct ggcggcgtgc ctaatacatg caagtcgagc ggacagatgg gagcttgctc     60
cctgatgtta gcggcggacg ggtgagtaac acgtgggtaa cctgcctgta agactgggat    120
aactccggga aaccggggct aataccggat gcttgtttga accgcatggt tcagacataa    180
aaggtggctt cggctaccac ttacagatgg acccgcggcg cattagctag ttggtgaggt    240
aacggctcac caaggcgacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga acaagtgccg ttcaaatagg cggcacctt gacggtacct aaccagaaag    480
ccacggctaa ctacgtgcca gcagccgcgg taatacgtag gtggcaagcg ttgtccggaa    540
ttattgggcg taaagggctc gcaggcggtt tcttaagtct gatgtgaaag ccccggctc    600 aaccggggag ggtcattgga aactgggaa cttgagtgca gaagaggaga gtggaattcc    660
acgtgtagcg gtgaaatgcg tagagatgtg gaggaacacc agtggcgaag gcgactctct    720
ggtctgtaac tgacgctgag gagcgaaagc gtggggagcg aacaggatta gatacccctgg    780 tagtccacgc cgtaaacgat gagtgctaag tgttagggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct cggggggcag   1020
agtgacaggt ggtgcatggt tgtcgtcagc tcgtgtcgtg agatgttggg ttaagtcccg   1080
caacgagcgc aaccccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat gggcagaaca agggcagcg aaaccgcgag gttaagccaa   1260
```

| tcccacaaat ctgttctcag ttcggatcgc agtctgcaac tcgactgcgt gaagctggaa | 1320 |
| tcgctagtaa tcgcggatca gcatgccgcg gtgaatacgt tcccgggcct tgtacacacc | 1380 |
| gcccgtcaca ccacgagagt ttgtaacacc cgaagtcggt gaggtaacct ttttggagcc | 1440 |
| agccgccgaa ggtgggacag atgattgggg tg | 1472 |

<210> SEQ ID NO 6
<211> LENGTH: 1507
<212> TYPE: DNA
<213> ORGANISM: Bacillus subtilis

<400> SEQUENCE: 6

| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactgggat | 120 |
| aactccggga aaccggggct aataccggat ggttgtttga accgcatggt tcaaacataa | 180 |
| aaggtggctt cggctaccac ttacagatgg acccgcggcg cattagctag ttggtgaggt | 240 |
| aacggctcac caaggcaacg atgcgtagcc gacctgagag ggtgatcggc cacactggga | 300 |
| ctgagacacg gcccagactc ctacgggagg cagcagtagg gaatcttccg caatggacga | 360 |
| aagtctgacg gagcaacgcc gcgtgagtga tgaaggtttt cggatcgtaa agctctgttg | 420 |
| ttagggaaga acaagtaccg ttcgaatagg gcggtacctt gacggtacct aaccagaaag | 480 |
| ccacggctaa ctacgtgcca gcagccgcgg taatacgtag gtggcaagcg ttgtccggaa | 540 |
| ttattgggcg taaagggctc gcaggcggtt tcttaagtct gatgtgaaag ccccggctc | 600 |
| aaccggggag ggtcattgga aactgggaa cttgagtgca gaagaggaga gtggaattcc | 660 |
| acgtgtagcg gtgaaatgcg tagagatgtg aggaacacc agtggcgaag gcgactctct | 720 |
| ggtctgtaac tgacgctgag gagcgaaagc gtggggagcg aacaggatta gataccctgg | 780 |
| tagtccacgc cgtaaacgat gagtgctaag tgttagggg tttccgcccc ttagtgctgc | 840 |
| agctaacgca ttaagcactc cgcctgggga gtacggtcgc aagactgaaa ctcaaaggaa | 900 |
| ttgacggggg cccgcacaag cggtggagca tgtggtttaa ttcgaagcaa cgcgaagaac | 960 |
| cttaccaggt cttgacatcc tctgacaatc ctagagatag gacgtcccct tcggggcag | 1020 |
| agtgacaggt ggtgcatggt tgtcgtcagc tcgtgtcgtg agatgttggg ttaagtcccg | 1080 |
| caacgagcgc aacccttgat cttagttgcc agcattcagt tgggcactct aaggtgactg | 1140 |
| ccggtgacaa accggaggaa ggtggggatg acgtcaaatc atcatgcccc ttatgacctg | 1200 |
| ggctacacac gtgctacaat ggacagaaca aagggcagcg aaaccgcgag gttaagccaa | 1260 |
| tcccacaaat ctgttctcag ttcggatcgc agtctgcaac tcgactgcgt gaagctggaa | 1320 |
| tcgctagtaa tcgcggatca gcatgccgcg gtgaatacgt tcccgggcct tgtacacacc | 1380 |
| gcccgtcaca ccacgagagt ttgtaacacc cgaagtcggt gaggtaacct tttaggagcc | 1440 |
| agccgccgaa ggtgggacag atgattgggg tgaagtcgta acaaggtagc cgtatcggaa | 1500 |
| ggtgcgg | 1507 |

<210> SEQ ID NO 7
<211> LENGTH: 1472
<212> TYPE: DNA
<213> ORGANISM: Bacillus amyloliquefaciens

<400> SEQUENCE: 7

| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactgggat | 120 |

```
aactccggga aaccggggct aataccggat gcttgtttga accgcatggt tcagacataa    180
aaggtggctt cggctaccac ttacagatgg acccgcggcg cattagctag ttggtgaggt    240
aacggctcac caaggcgacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga caagtgccg ttcaaatagg gcggcacctt gacggtacct aaccagaaag    480
ccacggctaa ctacgtgcca gcagccgcgg taatacgtag gtggcaagcg ttgtccggaa    540
ttattgggcg taaagggctc gcaggcggtt tcttaagtct gatgtgaaag cccccggctc    600
aaccggggag ggtcattgga aactgggaa cttgagtgca aagaggaga gtggaattcc    660 acgtgtagcg gtgaaatgcg tagagatgtg gaggaacacc agtggcgaag gcgactctct    720
ggtctgtaac tgacgctgag gagcgaaagc gtggggagcg aacaggatta gataccctgg    780
tagtccacgc cgtaaacgat gagtgctaag tgttaggggg ttttccgcccc ttagtgctgc    840 agctaacgca ttaagcactc cgcctgggga gtacggtcgc aagactgaaa ctcaaaggaa    900 ttgacgggg cccgcacaag cggtggagca tgtggtttaa ttcgaagcaa cgcgaagaac    960
cttaccaggt cttgacatcc tctgacaatc ctagagatag gacgtcccct tcggggcag   1020 agtgacaggt ggtgcatggt tgtcgtcagc tcgtgtcgtg agatgttggg ttaagtcccg   1080
caacgagcgc aacccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat gggcagaaca aagggcagcg aaaccgcgag gttaagccaa   1260
tcccacaaat ctgttctcag ttcggatcgc agtctgcaac tcgactgcgt gaagctggaa   1320
tcgctagtaa tcgcggatca gcatgccgcg gtgaatacgt tcccgggcct tgtacacacc   1380
gcccgtcaca ccacgagagt ttgtaacacc cgaagtcggt gaggtaacct ttttggagcc   1440
agccgccgaa ggtgggacag atgattgggg tg                                 1472
```

<210> SEQ ID NO 8
<211> LENGTH: 19
<212> TYPE: DNA
<213> ORGANISM: Artificial
<220> FEATURE:
<223> OTHER INFORMATION: PCR primer

<400> SEQUENCE: 8
gagtttgatc ctggctcag                                                  19

<210> SEQ ID NO 9
<211> LENGTH: 20
<212> TYPE: DNA
<213> ORGANISM: Artificial
<220> FEATURE:
<223> OTHER INFORMATION: PCR primer

<400> SEQUENCE: 9
agaaaggagg tgatccagcc                                                 20

<210> SEQ ID NO 10
<211> LENGTH: 21
<212> TYPE: DNA
<213> ORGANISM: Artificial
<220> FEATURE:
<223> OTHER INFORMATION: PCR Primer -continued

```
<400> SEQUENCE: 10
atctaatcct gtttgctccc c                                              21

<210> SEQ ID NO 11
<211> LENGTH: 15
<212> TYPE: DNA
<213> ORGANISM: Artificial
<220> FEATURE:
<223> OTHER INFORMATION: PCR primer

<400> SEQUENCE: 11
tacgggaggc agcag                                                     15

<210> SEQ ID NO 12
<211> LENGTH: 17
<212> TYPE: DNA
<213> ORGANISM: Artificial
<220> FEATURE:
<223> OTHER INFORMATION: PCR Primer

<400> SEQUENCE: 12
cggtgtgtrc aaggccc                                                   17

<210> SEQ ID NO 13
<211> LENGTH: 16
<212> TYPE: DNA
<213> ORGANISM: Artificial
<220> FEATURE:
<223> OTHER INFORMATION: PCR Primer

<400> SEQUENCE: 13
caacgagcgc aaccct                                                    16
```

BACILLUS STRAINS IMPROVING HEALTH AND PERFORMANCE OF PRODUCTION ANIMALS

CROSS-REFERENCE TO RELATED APPLICATIONS

This application is a 35 U.S.C. 371 national application of international application no. PCT/US2016/014492, filed Jan. 22, 2016, which claims priority or the benefit under 35 U.S.C. 119 of U.S. provisional application Nos. 62/106,869, 62/109,210, and 62/260,892, filed on Jan. 23, 2015, Jan. 29, 2015, and Nov. 30, 2015, respectively. The content of each of the aforementioned applications is fully incorporated herein by reference.

REFERENCE TO A DEPOSIT OF BIOLOGICAL MATERIAL

This application contains a reference to a deposit of biological material, which deposit is incorporated herein by reference.

REFERENCE TO SEQUENCE LISTING

This application contains a Sequence Listing in computer readable form. The computer readable form is incorporated herein by reference.
Index to sequence listing:
SEQ ID NO: 1 is 16S rDNA of DSM 29869.
SEQ ID NO: 2 is 16S rDNA of DSM 29870.
SEQ ID NO: 3 is 16S rDNA of DSM 29871.
SEQ ID NO: 4 is 16S rDNA of DSM 29872.
SEQ ID NO: 5 is 16S rDNA of *Bacillus vallismortis* from AB021198.
SEQ ID NO: 6 is 16S rDNA of *Bacillus subtilis* from AJ276351.
SEQ ID NO: 7 is 16S rDNA of *Bacillus amyloliquefaciens* from AB255669.
SEQ ID NO: 8 to SEQ ID NO: 13: PCR and sequencing primers.

BACKGROUND OF THE INVENTION

Field of the Invention

The present invention relates to an animal feed or an animal feed additive comprising *Bacillus* strains which improve the health and performance of production animals. The invention further relates use of the *Bacillus* strains in animal feed and animal feed additives.

Background of the Invention

*Clostridium perfringens* (*C. perfringens*) is a Gram-positive, rod-shaped, anaerobic, spore-forming bacterium of the genus *Clostridium*. *C. perfringens* is widely present in nature and can be found as a component of decaying vegetation, marine sediment, the intestinal tract of humans and other vertebrates, insects, and soil.

Infections due to *C. perfringens* show evidence of tissue necrosis, bacteremia, emphysematous cholecystitis, and gas gangrene, which is also known as clostridial myonecrosis. *C. perfringens* can also result in polymicrobial anaerobic infections.

The incidence of *Clostridium perfringens*-associated necrotic enteritis in poultry has increased in countries that stopped using antibiotic growth promoters. Necrotic enteritis is an enterotoxemic disease that results in significant economic losses in the poultry industry.

There is a need to develop tools and strategies for the prevention and control of *C. perfringens* in mono-gastric animals such as poultry. Whilst the vaccination of animals has been suggested, there are challenges associated with vaccinating thousands of animals. Thus discovering a solution which could be administered as an additive in an animal feed would be advantageous.

It is thus an object of the invention to provide solutions which prevents and/or controls *C. perfringens* in mono-gastric animals such as poultry by use of an animal feed comprising one or more bacteria with activity against *Clostridium perfringens*.

A further object of the invention is to provide a solution that does not present a risk for the health of the animal. The solution to this problem is use of non-hemolytic *Bacillus* strains with activity against *Clostridium perfringens*.

DESCRIPTION OF THE RELATED ART

Knap et al. (2010) describes that *Bacillus licheniformis* has an effect on necrotic enteritis in broiler chickens (Knap, Lund, Kehlet, Hofacre, and Mathis; *Bacillus licheniformis* Prevents Necrotic Enteritis in Broiler Chickens; Avian Diseases 54(2):931-935. 2010). This *Bacillus licheniformis* strain has no effect on *Clostridium perfringens* in vitro as demonstrated in Example 2.

Clostat (alias *Bacillus* PB6) is described in WO2007/064741. *Bacillus* PB6 has antagonistic effect against *C. perfringens*. *Bacillus* PB6 is hemolytic as described in Example 1.

SUMMARY OF THE INVENTION

It has been surprisingly found that the addition of direct fed microbes (DFM) from *Bacillus* species to animal feed can be used to prevent and/or control *C. perfringens* infections and/or necrotic enteritis in mono-gastric animal such as pigs and/or poultry. The *Bacillus* species can also improve the body weight gain and/or feed conversion rate (in both *Clostridium perfringens* challenged and unchallenged chickens).

In a first aspect the invention relates to an animal feed or an animal feed additive comprising a *Bacillus* strain characterized in that:
i) the *Bacillus* strain is non-hemolytic,
ii) the *Bacillus* strain has antimicrobial activity against *Clostridium perfringens* and
iii) the *Bacillus* strain improves body weight gain and/or feed conversion rate in chickens fed with the *Bacillus* strain.

In a second aspect the invention relates to an animal feed or an animal feed additive comprising a *Bacillus* strain characterized in that:
i) the *Bacillus* strain is non-hemolytic,
ii) the *Bacillus* strain has antimicrobial activity against *Clostridium perfringens* and
iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.

In a third aspect the invention relates to an animal feed or an animal feed additive comprising a *Bacillus* strain characterized in that:
i) the *Bacillus* strain is non-hemolytic, ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and iii) the *Bacillus* strain improves body weight gain and/or feed conversion rate in chickens fed with the *Bacillus* strain.

In a fourth aspect the invention relates to an animal feed or an animal feed additive comprising a *Bacillus* strain characterized in that:

i) the *Bacillus* strain is non-hemolytic, ii) the *Bacillus* strain has antimicrobial activity against *Clostridium perfringens* and iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.

The present invention relates to animal feed or animal feed additive comprising one or more of the *Bacillus* strains according to the invention which improves health and performance of production animals.

Methods of feeding an animal with the animal feed or animal feed additive according to the invention and methods of treating a *Clostridium perfringens* infection and/or for treating necrotic enteritis in an animal is also part of the invention. Use of the animal feed or animal feed additive according to the invention to improve the performance of an animal, such as improving the feed conversion rate, improving the body weight gain and/or improving the feed efficiency and/or improving the health is also part of this invention.

The invention further relates to a method for preventing and/or controlling *C. perfringens* infections and/or necrotic enteritis in a mono-gastric animal such as swine or poultry by use of an animal feed, wherein the animal feed comprises one or more *Bacillus* strains selected from the group consisting of the strain having the deposit accession number DSM 29869, DSM 29870, DSM 29871, and DSM 29872, or any combination thereof, wherein the *Bacillus* strain has antimicrobial activity against *Clostridium perfringens* and/or *E. coli*.

In an embodiment, the invention relates to an animal feed that is fed to a mono-gastric animal such as poultry or swine; comprising one or more *Bacillus* strains selected from the group consisting of the strain having the deposit accession number DSM 29869, DSM 29870, DSM 29871, and DSM 29872, or any combination thereof, wherein the *Bacillus* strain has antimicrobial activity against *Clostridium perfringens* and/or *E. coli*.

In a preferred embodiment the invention relates to an animal feed or an animal feed additive comprising a *Bacillus* strain wherein:

i. the *Bacillus* strain is selected from the group consisting of:

the strain having the deposit accession number DSM 29869; a strain having all of the identifying characteristics of *Bacillus* DSM 29869 or a mutant thereof, the strain having the deposit accession number DSM 29870; a strain having all of the identifying characteristics of *Bacillus* DSM 29870 or a mutant thereof, the strain having the deposit accession number DSM 29871; a strain having all of the identifying characteristics of *Bacillus* DSM 29871 or a mutant thereof, the strain having the deposit accession number DSM 29872; and a strain having all of the identifying characteristics of *Bacillus* DSM 29872 or a mutant thereof, and ii. the *Bacillus* strain has antimicrobial activity against *Clostridium perfringens* (such as *Clostridium perfringens* strains 23 or 48 [Gholamiandekhordi A R, Ducatelle R, Heyndrickx M, Haesebrouck F, Van Immerseel F. 2006. Molecular and phenotypical characterization of *Clostridium perfringens* isolates from poultry flocks with different diseasestatus. Vet. Microbiol. 113:143-152] and/or *E. coli* (such as ATCC10536 or ATCC25922).

In a further aspect, the invention relates to a method for preventing and/or controlling *C. perfringens* infections and/or necrotic enteritis in an animal such as pigs or poultry, comprising the steps of:

(a) feeding an animal such as a pig or poultry; and (b) administering to an animal such as pigs or poultry one or more *Bacillus* strains or spores of said strains selected from the group consisting of the strain having the deposit accession number DSM 29869; a strain having all of the identifying characteristics of *Bacillus* DSM 29869 or a mutant thereof, the strain having the deposit accession number DSM 29870; a strain having all of the identifying characteristics of *Bacillus* DSM 29870 or a mutant thereof, the strain having the deposit accession number DSM 29871; a strain having all of the identifying characteristics of *Bacillus* DSM 29871 or a mutant thereof, and the strain having the deposit accession number DSM 29872; a strain having all of the identifying characteristics of *Bacillus* DSM 29872 or a mutant thereof, or any combination thereof, wherein the *Bacillus* strain has antimicrobial activity against *Clostridium perfringens* and/or *E. coli*, and wherein step (a) occurs before, after, or simultaneously with step (b).

In an embodiment, the method relates to an animal feed that is fed to a mono-gastric animal such as pigs and/or poultry. The poultry can e.g. be chickens (such as broilers and/or layers).

In an embodiment, the animal feed or animal feed additive comprises one of more additional bacteria; is fed to a mono-gastric animal such as pigs and/or poultry; and further comprises concentrate and/or one or more enzymes and/or one or more additional microbes and/or one or more vitamins and/or one or more minerals and/or one or more amino acids and/or one or more other feed ingredients.

DEFINITIONS

Figure 1A:
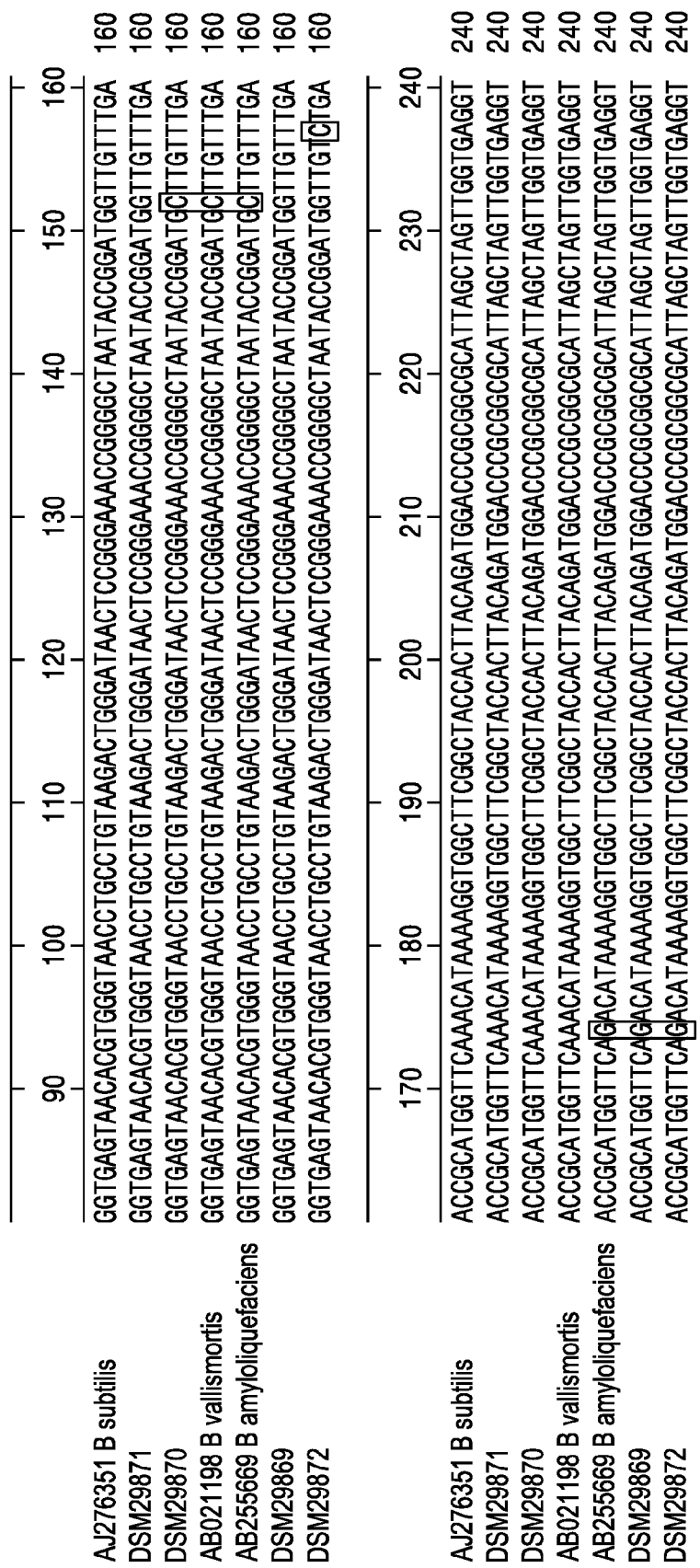
FIG. 1 Alignment of 16 S rDNA sequences. SEQ ID NO: 1 (DSM 29869), SEQ ID NO: 2 (DSM 29870), SEQ ID NO: 3 (DSM 29871), SEQ ID NO: 4 (DSM 29872), SEQ ID NO: 5 (*Bacillus vallismortis* AB021198), SEQ ID NO: 6 (*Bacillus subtilis* from AJ276351), and SEQ ID NO: 7 (*Bacillus amyloliquefaciens* AB255669) have been aligned. The region covering position 481-1200 is not shown in FIG. 1 (in this region all sequences are identical).

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms "a", "an" and "the" are intended to include the plural forms as well, unless the context clearly indicates otherwise.

Animal feed: The term "animal feed" refers to any compound, preparation, or mixture suitable for, or intended for intake by an animal. Animal feed for a mono-gastric animal comprises concentrates as well as for example vitamins, minerals, enzymes, amino acids and/or other feed ingredients (such as in a premix). The animal feed may further comprise forage. An example of poultry feed is given in Example 7.

Antimicrobial activity against *Clostridium perfringens*: The term "Antimicrobial activity against *Clostridium perfringens*" means that the growth of *Clostridium perfringens* is inhibited and/or that some or all of the *Clostridium perfringens* are killed. This can be determined by the assay described in Example 2.

Blend: the term "blend" means more than one of the bacterial strains described herein.

Body Weight Gain: The Body Weight Gain of an animal is the increase of body weight of the animal over a specified time period. An example of Body Weight Gain determination is given in Example 8.

Composition: The term "composition" refers to a composition comprising a carrier and at least one bacterial strain as described herein. The compositions described herein may be mixed with an animal feed(s) and referred to as a "mash feed."

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control *C. perfringens* infections and/or necrotic enteritis: The term "control *C. perfringens* infections and/or necrotic enteritis" means a method and/or composition that partly or completely inhibits *C. perfringens* infections and/or necrotic enteritis in an animal. Accordingly, the term "control *C. perfringens* infections and/or necrotic enteritis" means the *C. perfringens* infections and/or the necrotic enteritis is reduced or completely eliminated.

Direct Fed Microbial: The term "direct fed microbial" means live micro-organisms including spores which, when administered in adequate amounts, confer a benefit, such as improved digestion or health, on the host.

Enzymatic activity under aerobic conditions: The term "enzymatic activity under aerobic conditions" means that the polypeptides produced by a *Bacillus* strain during growth under aerobic conditions have one of more enzyme activities. The substrates tested are amylose, arabinan, cellulose, casein, arabinoxylan and xylan and degradation of the substrate indicates amylase, arabinase, cellulase, protease or xylanase activity respectively. Such an assay is performed as described in Example 6.

Enzymatic activity under anaerobic conditions: The term "enzymatic activity under anaerobic conditions" means activity of enzymes produced by a *Bacillus* strain during growth under anaerobic conditions as described in Example 6.

European Production Efficacy Factor (EPEF): The European Production Efficacy Factor is a way of comparing the live-bird performance of flocks. This single-figure facilitates comparison of performance within and among farms and can be used to assess environmental, climatic and managemental variables. The EPEF is calculated as [(liveability (%)× Liveweight (kg))/(Age at depletion (days)×FCR)]×100, wherein livability is the percentage of birds alive at slaughter, Liveweight is the average weight of the birds at slaughter, age of depletion is the age of the birds at slaughter and FCR is the feed conversion ratio at slaughter.

Effective amount/concentration/dosage: The terms "effective amount", "effective concentration", or "effective dosage" are defined as the amount, concentration, or dosage of the bacterial strain(s) sufficient to improve the digestion or yield of an animal. The actual effective dosage in absolute numbers depends on factors including: the state of health of the animal in question, other ingredients present. The "effective amount", "effective concentration", or "effective dosage" of the bacterial strains may be determined by routine assays known to those skilled in the art. An example of an effective amount for poultry is given in Example 7.

FCR (Feed Conversion Rate): FCR is a measure of an animal's efficiency in converting feed mass into increases of the desired output. Animals raised for meat—such as swine, poultry and fish—the output is the mass gained by the animal. Specifically FCR is the mass of the food eaten divided by the output, all over a specified period. FCR can be determined as described in Example 8. Improvement in FCR means reduction of the FCR value. A FCR improvement of 2% means that the FCR was reduced by 2%.

Feeding an animal: The terms "feeding an animal" or "fed to an animal" means that the composition of the present invention is administered orally to the animal one or more times in an effective amount. The oral administration is typically repeated e.g. one or more times daily over a specified time period such as several days, one week, several weeks, one months or several months. Feeding of poultry can e.g. be performed as described in Example 7.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, *brassica* (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Isolated: The term "isolated" means that the one or more bacterial strains described herein are in a form or environment which does not occur in nature, that is, the one or more bacterial strains are at least partially removed from one or more or all of the naturally occurring constituents with which it is associated in nature.

Non-hemolytic: Hemolysis is the breakdown of red blood cells. The ability of bacterial colonies to induce hemolysis when grown on blood agar is used to classify bacterial strains into hemolytic and non-hemolytic strains. In this context hemolysis is defined as described in EFSA Journal 2011; 9(11):2445, using *Bacillus subtilis* 168 (BGSC-1A1, *Bacillus* Genetic Stock Center) as a negative control. A *Bacillus* strain can be classified as non-hemolytic using the assay described in Example 1.

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Poultry: The term "poultry" means domesticated birds kept by humans for the eggs they produce and/or their meat and/or their feathers. Poultry includes broilers and layers. Poultry include members of the superorder Galloanserae (fowl), especially the order Galliformes (which includes chickens, Guineafowls, quails and turkeys) and the family Anatidae, in order Anseriformes, commonly known as "waterfowl" and including domestic ducks and domestic geese. Poultry also includes other birds that are killed for their meat, such as the young of pigeons. Examples of poultry include chickens (including layers, broilers and chicks), ducks, geese, pigeons, turkeys and quail.

Prevent *C. perfringens* infections and/or necrotic enteritis: The term "prevent *C. perfringens* infections and/or necrotic enteritis" means a method and/or composition that prevents development of a *C. perfringens* infection and/or necrotic enteritis in an animal.

Roughage: The term "roughage" means dry plant material with high levels of fiber, such as fiber, bran, husks from seeds and grains and crop residues (such as stover, copra, straw, chaff, sugar beet waste).

Sensitive to antibiotics: The term "sensitive to antibiotics" means the phenotypic property of a bacterial strain, that growth of said bacterial strain is inhibited under conditions where the bacterial strain would otherwise grow. In this context sensitivity to antibiotics is tested after the CLSI guidelines (M07-A9 Methods for Dilution Antimicrobial Susceptibility Tests for Bacteria That Grow Aerobically; 2012). The *S. aureus* ATCC 29213 is used as reference strain, which means that it should be included in the test, and that the results are only valid if *S. aureus* ATCC 29213 show results in compliance with the breakpoints of the CLSI guideline (see example Table 5.5) (M100-S24 Performance Standards for Antimicrobial Susceptibility Testing; informational Supplement, 2014). A strain of *Bacillus* is considered sensitive if the growth is detected at or below the breakpoint concentration of the appropriate antibiotic specified in EFSA journal 2012; 10(6):2740.

Silage: The term "silage" means fermented, high-moisture stored fodder which can be fed to ruminants (cud-chewing animals such as cattle and sheep) or used as a biofuel feedstock for anaerobic digesters. It is fermented and stored in a process called ensilage, ensiling or silaging, and is usually made from grass or cereal crops (e.g. maize, sorghum, oats, rye, timothy etc. forage grass plants),) or legume crops like clovers/trefoils, alfalfa, vetches, using the entire green plant (not just the grain). Silage can be made from many field crops, and special terms may be used depending on type (oatlage for oats, haylage for alfalfa). Silage is made either by placing cut green vegetation in a silo, by piling it in a large heap covered with plastic sheet, or by wrapping large bales in plastic film.

Spore: The terms "spore" and "endospore" are interchangeable and have their normal meaning which is well known and understood by those of skill in the art. As used herein, the term spore refers to a microorganism in its dormant, protected state.

Stable: The term "stable" is a term that is known in the art, and in a preferred aspect, stable is intended to mean the ability of the microorganism to remain in a spore form until it is administered to an animal to improve the health of the animal.

Swine: The term "swine" or "pigs" means domesticated pigs kept by humans for food, such as their meat. Swine includes members of the genus *Sus*, such as *Sus scrofa domesticus* or *Sus domesticus* and include piglets, growing pigs, and sows.

Vegetable protein: The term "vegetable protein" refers to any compound, preparation or mixture that includes at least one protein derived from or originating from a vegetable, including modified proteins and protein-derivatives.

DETAILED DESCRIPTION OF THE INVENTION

It has been surprisingly found that the addition of direct fed microbes (DFM) from *Bacillus* species to animal feed can be used to prevent and/or control *C. perfringens* infections and/or necrotic enteritis in mono-gastric animal such as pigs and/or poultry and at the same time improve the body weight gain and/or feed conversion rate (in both *C. perfringens* challenged and unchallenged chickens).

Animal Feed and Animal Feed Additive According to the Invention

The invention relates to an animal feed or an animal feed additive comprising spores of one or more *Bacillus* strains according to invention.

More specifically the invention relates to the following aspects with respect to an animal feed or an animal feed additive comprising *Bacillus* strains:

Aspect 1: An animal feed or an animal feed additive comprising spores of a *Bacillus* strain characterized in that:

i) the *Bacillus* strain is non-hemolytic, ii) the *Bacillus* strain has antimicrobial activity against *Clostridium perfringens* and iii) the *Bacillus* strain improves body weight gain and/or feed conversion rate in chickens fed with the *Bacillus* strain.

Aspect 2: An animal feed or an animal feed additive comprising spores of a *Bacillus* strain characterized in that:

i) the *Bacillus* strain is non-hemolytic, ii) the *Bacillus* strain has antimicrobial activity against *Clostridium perfringens* and iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.

Aspect 3: An animal feed or an animal feed additive comprising spores of a *Bacillus* strain characterized in that:

i) the *Bacillus* strain is non-hemolytic, ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and iii) the *Bacillus* strain improves body weight gain and/or feed conversion rate in chickens fed with the *Bacillus* strain.

Aspect 4: An animal feed or an animal feed additive comprising spores of a *Bacillus* strain characterized in that:

i) the *Bacillus* strain is non-hemolytic, ii) the *Bacillus* strain has antimicrobial activity against *Clostridium perfringens* and iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.

Sensitivity to Vancomycin, Clindamycin, Chloramphenicol, Gentamicin, Kanamycin, Streptomycin, Erythromycin and Tetracycline can e.g. be determined as described in Example 5.

Enzymatic activity under aerobic and/or anaerobic conditions that hydrolyzes one or more of the substrates selected from the group consisting of Amylose, Arabinan, Arabinoxylan, Casein and Xylan can e.g. be determined as described in Example 6.

In one embodiment the *Bacillus* strain of the animal feed or the animal feed additive according to Aspect 2, 3 or 4 has enzymatic activity under aerobic and/or anaerobic conditions that hydrolyzes one or more of the substrates selected from the group consisting of Amylose, Arabinan, Arabinoxylan, Casein and Xylan.

In one embodiment the *Bacillus* strain of the animal feed or the animal feed additive according to Aspect 1 or 3 improves one or more performance parameters in poultry selected from the list consisting of body weight gain, European Production Efficacy Factor and feed conversion rate in chickens fed with the *Bacillus* strain.

In one embodiment the *Bacillus* strain of the animal feed or the animal feed additive according to Aspect 4 has antimicrobial activity against *Clostridium perfringens*.

In one embodiment the *Bacillus* strain of the animal feed or the animal feed additive according to Aspect 1 or 2 is sensitive to at least seven such as eight of the antibiotics selected from the group consisting of Vancomycin, Clindamycin, Chloramphenicol, Gentamicin, Kanamycin, Streptomycin, Erythromycin and Tetracycline.

In one embodiment the improvement of feed conversion rate (FCR) for the animal feed or the animal feed additive of Aspect 1, 2, 3 or 4 results in a FCR of −2.5% or less than −2.5%, such as less than −2.6%, such as less than −2.7%, such as less than −2.8%, such less than −2.9%, such as less than −3.0%. In a preferred embodiment the improvement of FCR results in a FCR of from −5% to −2% such as a FRC from −4% to −2%, such as s FCR of from −3.5% to −2.5%. In a specific embodiment the improvement of FCR for Aspect 1, 2, 3 or 4 results in a FCR within an interval selected from the group consisting of from −5% to −4.5%, from −4.5% to −4%, from −4% to −3.8%, from −3.8% to −3.6%, from −3.6% to −3.4%, from −3.4% to −3.2%, from −3.2 to −3.0%, from −3.0% to −2.8% and from −2.8 to −2.5%, or any combination of these intervals. The FCR can be determined as described in Example 8.

In one embodiment the improvement in body weight gain for the animal feed or the animal feed additive of Aspect 1, 2, 3 or 4 results in a body weight gain of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment the improvement in body weight gain for Aspect 1, 2, 3 or 4 results in a body weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The body weight gain can be determined as described in Example 8.

In one embodiment the *Bacillus* strain of the animal feed or the animal feed additive according to Aspect 1, 2, 3 or 4 wherein the *Bacillus* strain comprises 16S rDNA that is more than 98% (such as more than 98.5%, such as more than 99%, such as more than 99.5%) sequence identity to SEQ ID NO: 1 and/or more than 98% (such as more than 98.5%, such as more than 99%, such as more than 99.5%) sequence identity to SEQ ID NO: 2 and/or more than 98% (such as more than 98.5%, such as more than 99%, such as more than 99.5%) sequence identity to SEQ ID NO: 3 and/or more than 98% (such as more than 98.5%, such as more than 99%, such as more than 99.5%) sequence identity to SEQ ID NO: 4.

In one embodiment the *Bacillus* strain of the animal feed or the animal feed additive according to Aspect 1, 2, 3 or 4 is a *Bacillus subtilis* strain, or a *Bacillus amyloliquefaciens* strain.

In one embodiment the *Bacillus* strain of the animal feed or the animal feed additive according to Aspect 1, 2, 3 or 4 has antimicrobial effect against *E. coli*. The effect against *E. coli* can e.g. be determined as described in Example 4.

In one embodiment the *Bacillus* strain of the animal feed or the animal feed additive according to Aspect 1, 2, 3 or 4 is the *Bacillus* strain having deposit accession number DSM 29869, or a strain having all of the identifying characteristics of *Bacillus* DSM 29869 or a mutant thereof that has antimicrobial activity against *Clostridium perfringens*. In another embodiment the *Bacillus* strain of the animal feed or the animal feed additive according to Aspect 1, 2, 3 or 4 is the *Bacillus* strain having deposit accession number DSM 29870, or a strain having all of the identifying characteristics of *Bacillus* DSM 29870 or a mutant thereof that has antimicrobial activity against *Clostridium perfringens*. In yet another embodiment the *Bacillus* strain of the animal feed or the animal feed additive according to Aspect 1, 2, 3 or 4 is the *Bacillus* strain having deposit accession number DSM 29871, or a strain having all of the identifying characteristics of *Bacillus* DSM 29871 or a mutant thereof that has antimicrobial activity against *Clostridium perfringens*. In a further embodiment the *Bacillus* strain of the animal feed or the animal feed additive according to Aspect 1, 2, 3 or 4 is the *Bacillus* strain having deposit accession number DSM 29872, or a strain having all of the identifying characteristics of *Bacillus* DSM 29872 or a mutant thereof that has antimicrobial activity against *Clostridium perfringens*.

The invention relates in one embodiment to an animal feed or an animal feed additive comprising a *Bacillus* having deposit accession number DSM 29869 or a strain having all of the identifying characteristics of *Bacillus* DSM 29869 or a mutant thereof. The invention relates in another embodiment to an animal feed or an animal feed additive comprising a *Bacillus* having deposit accession number DSM 29870 or a strain having all of the identifying characteristics of *Bacillus* DSM 29870 or a mutant thereof. The invention relates in another embodiment to an animal feed or an animal feed additive comprising a *Bacillus* having deposit accession number DSM 29871 or a strain having all of the identifying characteristics of *Bacillus* DSM 29871 or a mutant thereof. The invention relates in a further embodiment to an animal feed or an animal feed additive comprising a *Bacillus* having deposit accession number DSM 29872 or a strain having all of the identifying characteristics of *Bacillus* DSM 29872 or a mutant thereof.

In one embodiment of Aspect 1, 2, 3 or 4 the *bacillus* spores of the animal feed or the animal feed additive are present as dried spores. The animal feed or the animal feed additive according to Aspect 1, 2, 3 or 4 can also be a liquid composition and/or comprise culture supernatant comprising one or more *Bacillus* strain(s) of the invention.

In one embodiment of Aspect 1, 2, 3 or 4 the animal feed or the animal feed additive further comprises a carrier. The carrier can comprise one or more of the following compounds: water, glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch and cellulose.

In one embodiment the animal feed or the animal feed additive comprises one or more coccidiostats wherein the composition e.g. is a premix.

In a preferred embodiment the animal feed or the animal feed additive according to Aspect 1, 2, 3 or 4 comprises from 105 to $10^{12}$ CFU/g of isolated *Bacillus* spores.

In one embodiment the animal feed or animal feed additive is characterized in that at least 70% (such as at least 80% or at least 90%) of the *Bacillus* spores survive gastric stability in a mono-gastric animal such as chickens.

The animal feed or the animal feed additive according to Aspect 1, 2, 3 or 4 which further comprises one or more components selected from the list consisting of: one or more enzymes; one or more additional microbes; one or more vitamins; one or more minerals; one or more amino acids; and one or more other feed ingredients.

The animal feed according to Aspect 1, 2, 3 or 4 can be fed to an animal wherein the bacterial count of each *Bacillus* spore is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

In a preferred embodiment, the bacterial count of each of the bacterial strains in the animal feed additive is between $1\times10^7$ and $1\times10^{18}$ CFU/kg of composition, preferably between $1\times10^9$ and $1\times10^{16}$ CFU/kg of composition, more preferably between $1\times10^{10}$ and $1\times10^{15}$ CFU/kg of composition and most preferably between $1\times10^{11}$ and $1\times10^{14}$ CFU/kg of dry matter.

In a preferred embodiment the animal feed or the animal feed additive according to Aspect 1, 2, 3 or 4 can be an animal feed or an animal feed additive wherein the bacterial count of each *Bacillus* spore is between $1\times10^3$ and $1\times10^{13}$ CFU/animal/day, preferably between $1\times10^5$ and $1\times10^{11}$ CFU/animal/day, and more preferably between $1\times10^6$ and $1\times10^{10}$ CFU/animal/day and even more preferably between $1\times10^7$ and $1\times10^9$ CFU/animal/day.

The animal feed or the animal feed additive according to Aspect 1, 2, 3 or 4 can be a mono-gastric animal feed. The mono-gastric animal can be selected from the group consisting of pigs, swine, piglets, sows, poultry, turkeys, ducks, chicken, broilers, layers, chicks, fish and crustaceans. In one embodiment the animal is not a human being. Mono-gastric animals include in one embodiment, but are not limited to, pigs or swine (including, but not limited to, piglets, growing pigs, and sows); poultry such as turkeys, ducks and chicken (including but not limited to broilers, chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

In a preferred embodiment the animal feed or the animal feed additive according to Aspect 1, 2, 3 or 4 is an animal feed or animal feed additive wherein the *Bacillus* strain improves gut health of chickens infected with *Clostridium perfringens* e.g. by having antimicrobial activity against *Clostridium perfringens*.

In a preferred embodiment the animal feed or the animal feed additive according to Aspect 1, 2, 3 or 4 is an animal feed or animal feed additive for treatment of necrotic enteritis or treatment of a *Clostridium perfringens* infection (e.g. for treatment of mono-gastric animals including swine and poultry such as chickens).

In a further embodiment, the animal feed or animal feed additive comprises one or more bacterial strains such as at least two of the above strains up to and including all of the strains in the group consisting of DSM 29869, DSM 29870, DSM 29871 and DSM 29872.

In an embodiment to any of the aforementioned embodiments the *Bacillus* spore kills/inhibits at least 40% (such as at least 45%, at least 50%, at least 60%, at least 70% or at least 80%) of *Clostridium perfringens* after e.g. 24 hours e.g. determined as described in Example 2.

In another embodiment of the invention the animal feed or animal feed additive further comprises concentrate. In another embodiment of the invention the animal feed or animal feed additive further comprises forage. In another embodiment of the invention the animal feed or animal feed additive such as the animal feed further comprises one or more additional microbes. In another embodiment of the invention the animal feed or animal feed additive further comprises one or more enzymes. In another embodiment of the invention the animal feed or animal feed additive further comprises one or more vitamins. In another embodiment of the invention the animal feed or animal feed additive further comprises one or more minerals. In another embodiment of the invention the animal feed or animal feed additive such as the animal feed further comprises one or more amino acids. In another embodiment of the invention the animal feed or animal feed additive further comprises one or more other feed ingredients.

In an embodiment to any of the aforementioned embodiments, the animal feed or the animal feed additive also improves the health of the mono-gastric animal when fed to said animal. In another embodiment to any of the aforementioned embodiments, the animal feed or the animal feed additive also increases the egg yield of poultry when fed said poultry. In an embodiment to any of the aforementioned embodiments, the animal feed or the animal feed additive increases the meat yield of the mono-gastric animal when fed to said animal.

In a preferred embodiment, the animal feed comprises one or more bacterial strains described herein, wherein the bacterial count of each of the bacterial strains is between $1\times10^4$ and $1\times10^{14}$ CFU/kg of animal feed, preferably between $1\times10^6$ and $1\times10^{12}$ CFU/kg of animal feed, and more preferably between $1\times10^7$ and $1\times10^{11}$ CFU/kg of animal feed. In a more preferred embodiment the bacterial count of each of the bacterial strains described herein is between $1\times10^8$ and $1\times10^{10}$ CFU/kg of animal feed.

In a preferred embodiment, the animal feed additive comprises one or more bacterial strains described herein, wherein the bacterial count of each of the bacterial strains is between $1\times10^7$ and $1\times10^{18}$ CFU/kg of animal feed additive, preferably between $1\times10^9$ and $1\times10^{16}$ CFU/kg of animal feed additive, and more preferably between $1\times10^{10}$ and $1\times10^{15}$ CFU/kg of animal feed additive. In a more preferred embodiment the bacterial count of each of the bacterial strains described herein is between $1\times10^{11}$ and $1\times10^{14}$ CFU/kg of animal feed additive.

In a preferred embodiment, the bacterial count of each of the bacterial strains in the animal feed is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed is between $1\times10^8$ and $1\times10^{10}$ CFU/kg of dry matter.

In a more preferred embodiment the animal feed or the animal feed additive according to Aspect 1, 2, 3 or 4 can be an animal feed or an animal feed additive wherein the bacterial count of each *Bacillus* spore is between $1\times10^{13}$ and $1\times10^{13}$ CFU/animal/day, preferably between $1\times10^5$ and $1\times10^{11}$ CFU/animal/day, and more preferably between $1\times10^6$ and $1\times10^{10}$ CFU/animal/day and even more preferably between $1\times10^7$ and $1\times10^9$ CFU/animal/day.

In still yet another embodiment of the invention, the one or more bacterial strains are present in the animal feed or the animal feed additive in form of a spore such as a stable spore. In still a further embodiment of the invention, the stable spore will germinate in the intestine and/or stomach of the mono-gastric animal.

In one embodiment, the one or more bacterial strains are stable when subjected to pressures applied/achieved during an extrusion process for pelleting. In a particular embodiment, the one or more bacterial strains are stable at pressures ranging from 1 bar to bar, particularly 10 bar to 40 bar, more particularly 15 bar to 40 bar, even more particularly bar to 40 bar, still even more particularly 35 bar to 37 bar, even still more particularly 36 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 80° C. to 120° C., particularly temperatures ranging from, 90° C. to 120° C., even more particularly temperatures ranging from 95° C. to 120° C.

In another aspect, the invention relates to an animal feed or animal feed additive comprising a carrier, such as forage, and one or more of the bacteria cultures having characteristics substantially identical to that of a strain selected from the group consisting of:

the strain having the deposit accession number DSM 29869;

the strain having the deposit accession number DSM 29870;

the strain having the deposit accession number DSM 29871; and the strain having the deposit accession number DSM 29872; or any combination thereof.

In an embodiment, the animal feed or animal feed additive comprises a carrier and the strain having the deposit accession number DSM 29869, or a strain having all of the identifying characteristics of *Bacillus* DSM 29869 or a mutant thereof.

In an embodiment, the animal feed or animal feed additive comprises a carrier and the strain having the deposit accession number DSM 29870, or a strain having all of the identifying characteristics of *Bacillus* DSM 29870 or a mutant thereof.

In an embodiment, the animal feed or animal feed additive comprises a carrier and the strain having the deposit accession number DSM 29871, or a strain having all of the identifying characteristics of *Bacillus* DSM 29871 or a mutant thereof.

In an embodiment, the animal feed or animal feed additive comprises a carrier and the strain having the deposit accession number DSM 29872, or a strain having all of the identifying characteristics of *Bacillus* DSM 29872 or a mutant thereof.

In another embodiment, the animal feed or animal feed additive is for feeding to a mono-gastric animal. Mono-gastric animals include, but are not limited to, pigs or swine (including, but not limited to, piglets, growing pigs, and sows); poultry such as turkeys, ducks and chicken (including but not limited to broiler chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

In an embodiment, the animal feed or animal feed additive further comprises one or more additional microbes. In a particular embodiment, the animal feed further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a particular embodiment, animal feed or animal feed additive further comprises a bacterium from one or more of the following strains of *Bacillus amyloliquefaciens, Bacillus subtilis, Bacillus pumilus, Bacillus polymyxa, Bacillus licheniformis, Bacillus megaterium, Bacillus coagulans, Bacillus circulans*, or any combination thereof.

In a particular embodiment, the animal feed or animal feed additive further comprises one or more types of yeast. The one or more types of yeast can be selected from the group consisting of Saccharomycetaceae, *Saccharomyces* (such as *S. cerevisiae* and/or *S. boulardii*), *Kluyveromyces* (such as *K. marxianus* and *K. lactis*), *Candida* (such as *C. utilis*, also called *Torula* yeast), *Pichia* (such as *P. pastoris*), *Torulaspora* (such as *T. delbrueckii*), *Phaffia* yeasts and *Basidiomycota*.

In an embodiment to any of the aforementioned embodiments the animal feed or the animal feed additive further comprises a carrier. The carrier can comprise one or more of the following compounds: water, glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch and cellulose.

Animal Feed

In one aspect, the animal feed comprises the *Bacillus* strain according to Aspect 1, 2, 3 or 4 or the *Bacillus* strain having deposit accession number DSM 29869 and/or DSM 29870 and/or DSM 29871 and/or DSM 29872, or a strain having all of the identifying characteristics of *Bacillus* DSM 29869 and/or DSM 29870 and/or DSM 29871 and/or DSM 29872 or a mutant of DSM 29869 and/or DSM 29870 and/or DSM 29871 and/or DSM 29872 and further comprises one or more of concentrate(s), vitamin(s), mineral(s), enzyme(s), amino acid(s) and/or other feed ingredient(s). In a specific embodiment the animal feed further comprises forage.

Forage as defined herein also includes roughage. Forage is fresh plant material such as hay and silage from forage plants, grass and other forage plants, grass and other forage plants, seaweed, sprouted grains and legumes, or any combination thereof. Examples of forage plants are Alfalfa (lucerne), birdsfoot trefoil, *brassica* (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Crops suitable for ensilage are the ordinary grasses, clovers, alfalfa, vetches, oats, rye and maize. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Roughage is generally dry plant material with high levels of fiber, such as fiber, bran, husks from seeds and grains and crop residues (such as stover, copra, straw, chaff, sugar beet waste).

Examples of concentrates are feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

In one embodiment, the forage and one or more microbes are mixed with a concentrate. In another embodiment, the forage and one or more microbes are mixed with a premix. In a further embodiment, the forage and one or more microbes are mixed with vitamins and/or minerals. In a further embodiment, the forage and one or more microbes are mixed with one or more enzymes. In a further embodiment, the forage and one or more microbes are mixed with other feed ingredients, such as colouring agents, stabilisers, growth improving additives and aroma compounds/flavorings, polyunsaturated fatty acids (PUFAs); reactive oxygen generating species, anti-microbial peptides, anti-fungal polypeptides and amino acids.

In particular embodiments, the animal feed may comprise Bacillus stain DSM 29869 and/or DSM 29870 and/or DSM 29871 and/or DSM 29872 or a strain having all of the identifying characteristics of Bacillus DSM 29869 and/or DSM 29870 and/or DSM 29871 and/or DSM 29872 or a mutant of DSM 29869 and/or DSM 29870 and/or DSM 29871 and/or DSM 29872 and 0-80% maize; and/or 0-80% sorghum; and/or 0-70% wheat; and/or 0-70% barley; and/or 0-30% oats; and/or 0-40% soybean meal; and/or 0-10% fish meal; and/or 0-20% whey.

The animal feed may comprise Bacillus stain DSM 29869 and/or DSM 29870 and/or DSM 29871 and/or DSM 29872 or a strain having all of the identifying characteristics of Bacillus DSM 29869 and/or DSM 29870 and/or DSM 29871 and/or DSM 29872 or a mutant of DSM 29869 and/or DSM 29870 and/or DSM 29871 and/or DSM 29872 and vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

In a particular embodiment the animal feed consists of or comprises milk (e.g. from sow) e.g. for feeding of piglets. In another particular embodiment the animal feed consists of or comprises milk replacement e.g. for feeding of piglets.

Premix

In an embodiment, the animal feed may include a premix, comprising e.g. vitamins, minerals, enzymes, preservatives, antibiotics, other feed ingredients or any combination thereof which are mixed into the animal feed.

In one aspect, the invention related to a premix for feeding an animal infected by *Clostridium perfringens*, the premix comprising at least the *Bacillus* strain DSM 29870 described above.

In a further embodiment, the premix may comprise one or more bacterial strains, in addition to DSM 29870.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

Enzymes

In another embodiment, the animal feed or animal feed additive described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho, P. M. & Henrissat, B. (1999) Carbohydrate-Active Enzymes server at URL: http://afmb.cnrs-mrs.fr/~cazy/CAZY/index-.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation", K. Ohmiya, K. Hayashi, K. Sakka, Y. Kobayashi, S. Karita and T. Kimura eds., Uni Publishers Co., Tokyo, pp. 15-23).

Thus the animal feed or animal feed additive of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

In a particular embodiment, the animal feed or animal feed additive of the invention comprises a phytase (EC 3.1.3.8 or 3.1.3.26). Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in e.g. WO 98/28408, WO 00/43503, and WO 03/066847.

In a particular embodiment, the animal feed or animal feed additive of the invention comprises a xylanase (EC 3.2.1.8). Examples of commercially available xylanases include Ronozyme® WX and G2 (DSM Nutritional Products), Econase® XT and Barley (AB Vista), Xylathin® (Verenium) and Axtra® XB (Xylanase/beta-glucanase, DuPont).

In a particular embodiment, the animal feed or animal feed additive of the invention comprises a protease (EC 3.4). Examples of commercially available proteases include Ronozyme® ProAct (DSM Nutritional Products).

Amino Acids

The animal feed or animal feed additive of the invention may further comprise one or more amino acids. Examples of amino acids which are used in animal feed are lysine, alanine, beta-alanine, threonine, methionine and tryptophan.

Other Feed Ingredients

The animal feed or animal feed additive of the invention may further comprise colouring agents, stabilisers, growth improving additives and aroma compounds/flavorings, polyunsaturated fatty acids (PUFAs); reactive oxygen generating species, anti-microbial peptides and anti-fungal polypeptides.

Examples of colouring agents are carotenoids such as beta-carotene, astaxanthin, and lutein.

Examples of aroma compounds/flavorings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the Aspergillus giganteus, and Aspergillus niger peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The animal feed or animal feed additive of the invention may further comprise at least one amino acid. Examples of amino acids which are used in animal feed are lysine, alanine, beta-alanine, threonine, methionine and tryptophan.

Manufacturing

Animal diets can e.g. be manufactured as mash feed (non-pelleted) or pelleted feed. Typically, the milled feedstuffs are mixed and sufficient amounts of essential vitamins and minerals are added according to the specifications for the species in question. The bacteria cultures and optionally enzymes can be added as solid or liquid formulations. For example, for mash feed a solid or liquid culture formulation may be added before or during the ingredient mixing step. For pelleted feed the (liquid or solid) culture preparation may also be added before or during the feed ingredient step. Typically a liquid culture preparation comprises the culture of the invention optionally with a polyol, such as glycerol, ethylene glycol or propylene glycol, and is added after the pelleting step, such as by spraying the liquid formulation onto the pellets. The enzyme may also be incorporated in a feed additive or premix.

The enzyme may be added to the feed mix as a granule, which is optionally pelleted or extruded. The granule typically comprises a core particle and one or more coatings, which typically are salt and/or wax coatings. The core particle can either be a homogeneous blend of an active compound optionally together with salts (e.g. organic or inorganic zinc or calcium salt) or an inert particle with an active compound applied onto it. The active compound is the culture of the invention optionally combined with one or more enzymes. The inert particle may be water soluble or water insoluble, e.g. starch, a sugar (such as sucrose or lactose), or a salt (such as NaCl, $Na_2SO_4$). The salt coating is typically at least 1 µm thick and can either be one particular salt or a mixture of salts, such as $Na_2SO_4$, $K_2SO_4$, $MgSO_4$ and/or sodium citrate. Other examples are those described in e.g. WO 2008/017659, WO 2006/034710, WO 97/05245, WO 98/54980, WO 98/55599, WO 2000/70034 or polymer coating such as described in WO 2001/00042.

Methods of Treatment of C. perfringens Infections and/or Necrotic Enteritis

In one embodiment, the invention relates to a method for treatment of C. perfringens infections and/or necrotic enteritis in an animal such as a mono-gastric animal including poultry using the animal feed or animal feed additive according to Aspect 1, 2, 3 or 4. In a specific embodiment the invention relates to a method for treatment of C. per-

*fringens* infections and/or necrotic enteritis in an animal such as an mono-gastric animal including poultry using an animal feed or animal feed additive comprising the *Bacillus* strain having deposit accession number DSM 29869 and/or DSM 29870 and/or DSM 29871 and/or DSM 29872, or a strain having all of the identifying characteristics of *Bacillus* DSM 29869 and/or DSM 29870 and/or DSM 29871 and/or DSM 29872 or a mutant of DSM 29869 and/or DSM 29870 and/or DSM 29871 and/or DSM 29872.

In one embodiment the animal is not a human being. In a further embodiment, the animal feed is fed to a mono-gastric animal. Mono-gastric animals include, but are not limited to, pigs or swine (including, but not limited to, piglets, growing pigs, and sows); poultry such as turkeys, ducks and chicken (including but not limited to broiler chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

The animal feed can further comprise one or more components selected from the list consisting of concentrate; forage; one or more enzymes; one or more additional microbes; one or more vitamins; one or more minerals; one or more amino acids; and one or more other feed ingredients.

In a further embodiment, the method comprises adding to the animal feed one or more bacterial strains such as at least two of the above strains, at least three of the above strains, or up to and including all of the above strains.

In one embodiment, the method comprises adding to the animal feed the *Bacillus* strains having the deposit accession number DSM 29869 or a strain having all the identifying characteristics of *Bacillus* DSM 29869 or a mutant thereof.

In one embodiment, the method comprises adding to the animal feed the *Bacillus* strains having the deposit accession number DSM 29870 or a strain having all the identifying characteristics of *Bacillus* DSM 29870 or a mutant thereof.

In one embodiment, the method comprises adding to the animal feed the *Bacillus* strains having the deposit accession number DSM 29871 or a strain having all the identifying characteristics of *Bacillus* DSM 29871 or a mutant thereof.

In one embodiment, the method comprises adding to the animal feed the *Bacillus* strains having the deposit accession number DSM 29872 or a strain having all the identifying characteristics of *Bacillus* DSM 29872 or a mutant thereof.

In another embodiment of the method, the animal feed further comprises concentrate. In another embodiment of the method, the animal feed further comprises forage. In another embodiment of the method, the animal feed further comprises one or more additional microbes. In another embodiment of the method, the animal feed further comprises one or more enzymes. In another embodiment of the method, the animal feed further comprises one or more vitamins. In another embodiment of the method, the animal feed further comprises one or more minerals. In another embodiment of the method, the animal feed further comprises one or more amino acids. In another embodiment of the method, the animal feed further comprises one or more other feed ingredients.

In an embodiment to any of the aforementioned embodiments, the method also improves the health of the mono-gastric animal feed. In another embodiment to any of the aforementioned embodiments, the method also increases the egg yield of poultry. In an embodiment to any of the aforementioned embodiments, the method also increases the meat yield of the mono-gastric animal.

In a preferred embodiment, the method comprises administering to a mono-gastric animal one or more bacterial strains described herein, wherein the bacterial count of each of the bacterial strains is between $1\times10^4$ and $1\times10^{14}$ CFU/kg of forage, preferably between $1\times10^6$ and $1\times10^{12}$ CFU/kg of forage, and more preferably between $1\times10^7$ and $1\times10^{11}$ CFU/kg of animal feed. In a more preferred embodiment the bacterial count of each of the bacterial strains described herein is between $1\times10^8$ and $1\times10^{10}$ CFU/kg of animal feed.

In a preferred embodiment, the method comprises administering to a mono-gastric animal one or more bacterial strains described herein, wherein the bacterial count of each of the bacterial strains is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains described herein is between $1\times10^9$ and $1\times10^{11}$ CFU/animal/day.

In another aspect, the invention covers the method for treatment of *C. perfringens* infections comprising:
  (a) feeding a mono-gastric animal a feed; and
  (b) administering to an animal one or more *Bacillus* strains selected from the group consisting of:
    (i) the strain having the deposit accession number DSM 29869; or a strain having all the identifying characteristics of *Bacillus* DSM 29869 or a mutant thereof;
    (ii) the strain having the deposit accession number DSM 29870; or a strain having all the identifying characteristics of *Bacillus* DSM 29870 or a mutant thereof;
    (iii) the strain having the deposit accession number DSM 29871; or a strain having all the identifying characteristics of *Bacillus* DSM 29871 or a mutant thereof; and/or
    (iv) the strain having the deposit accession number DSM 29872; or a strain having all the identifying characteristics of *Bacillus* DSM 29872 or a mutant thereof or any combination thereof,
  wherein the *Bacillus* strain antimicrobial activity against *Clostridium perfringens* and/or *E. coli*, and wherein step (a) occurs before, after, or simultaneously with step (b).

In a further embodiment, the method comprises administering to the animal feed one or more bacterial strains such as at least two of the above strains, at least three of the above strains, or up to and including all of the above strains.

In a preferred embodiment of the method, the animal feed is fed to a mono-gastric animal. In an embodiment of the method, the mono-gastric animal is e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), or fish (including but not limited to salmon, trout, tilapia, catfish and carps; and crustaceans (including but not limited to shrimps and prawns).

In another embodiment of the method, the animal feed further comprises one or more components selected from the list consisting of concentrate; forage; one or more enzymes; one or more additional microbes; one or more vitamins; one or more minerals; one or more amino acids; and one or more other feed ingredients.

In another embodiment of the method, the animal feed further comprises concentrate. In another embodiment of the method, the animal feed further comprises forage. In another embodiment of the method, the animal feed further comprises one or more additional microbes. In another embodiment of the method, the animal feed further comprises one or more enzymes. In another embodiment of the method, the animal feed further comprises one or more vitamins. In another embodiment of the method, the animal feed further comprises one or more minerals. In another embodiment of the method, the animal feed further comprises one or more amino acids. In another embodiment of the method, the animal feed further comprises one or more other feed ingredients.

In still yet another embodiment of the method, the one or more bacterial strains are present in the form of a stable spore. In still a further embodiment of the method, the stable spore will germinate in the intestine and/or stomach of the mono-gastric animal.

In a preferred embodiment, the method comprises administering to a mono-gastric animal one or more bacterial strains described herein, wherein the bacterial count of each of the bacterial strains is between $1\times10^4$ and $1\times10^{14}$ CFU/kg of forage, preferably between $1\times10^6$ and $1\times10^{12}$ CFU/kg of forage, and more preferably between $1\times10^7$ and $1\times10^{11}$ CFU/kg of forage. In a more preferred embodiment the bacterial count of each of the bacterial strains described herein is between $1\times10^8$ and $1\times10^{10}$ CFU/kg of forage.

In a preferred embodiment, the method comprises administering to a mono-gastric animal one or more bacterial strains described herein, wherein the bacterial count of each of the bacterial strains is between $1\times10^5$ and $1\times10^{18}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains described herein is between $1\times10^9$ and $1\times10^{11}$ CFU/animal/day.

In a preferred embodiment, the method comprises administering to a mono-gastric animal one or more bacterial strains described herein, wherein the bacterial count of each *Bacillus* spore is between $1\times10^5$ and $1\times10^{15}$ CFU/animal/day, preferably between $1\times10^7$ and $1\times10^{13}$ CFU/animal/day, and more preferably between $1\times10^8$ and $1\times10^2$ CFU/animal/day.

The invention relates in a further embodiment to use of the animal feed or animal feed additive to improve the performance of an animal, such as improving the feed conversion rate and/or improving the European Production Efficacy Factor and/or improving the body weight gain and/or improving the feed efficiency and/or improving the health.

In one embodiment the improvement of feed conversion rate (FCR) for Aspect 1, 2, 3 or 4 results in a FCR of −2.5% or less than −2.5%, such as less than −2.6%, such as less than −2.7%, such as less than −2.8%, such less than −2.9%, such as less than −3.0%. In a preferred embodiment the improvement of FCR results in a FCR of from −5% to −2% such as a FCR from −4% to −2%, such as s FCR of from −3.5% to −2.5%. In a specific embodiment the improvement of FCR for Aspect 1, 2, 3 or 4 results in a FCR within an interval selected from the group consisting of from −5% to −4.5%, from −4.5% to −4%, from −4% to −3.8%, from −3.8% to −3.6%, from −3.6% to −3.4%, from −3.4% to −3.2%, from −3.2 to −3.0%, from −3.0% to −2.8% and from −2.8 to −2.5%, or any combination of these intervals. The FCR can be determined as described in Example 8.

In one embodiment the improvement in body weight gain for Aspect 1, 2, 3 or 4 results in a body weight gain of at least 0.5%, such as at least 0.8%, such as at least 1.5%, such as at least 1.8%, such as at least 2.0%, such as at least 2.3%, such as at least 3.5%, such as at least 4.2%, such as at least 5.2%, such as at least 6.5%, such as at least 7.3%. In a preferred embodiment the improvement in body weight gain for Aspect 1, 2, 3 or 4 results in a body weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof. The body weight gain can be determined as described in Example 8.

Animal Feed and Animal Feed Additive Comprising *Bacillus* DSM 29870 and Use Thereof The invention relates to the use of a feed or feed premix comprising at least the spores of a *Bacillus* subspecies to improve the performance of an animal infected by *C. perfringens*. More specifically the feed or feed premix described within the present comprise a *Bacillus* DSM29870 (hereafter DSM 29870). This strain is characterized in that is non-hemolytic, has antimicrobial activity e.g. against *Clostridium perfringens* and/or *E. coli*, is sensitive to Vancomycin, Clindamycin, Chloramphenicol, Gentamicin, Kanamycin, Streptomycin, Erythromycin and Tetracycline, improves body weight gain and/or feed conversion ratio in animal, hydrolyzes one or more of the substrates selected from the group consisting of amylase, arabinan, arabinoxylan, casein and xylan.

In an embodiment the present invention relates to the use of a feed or feed premix comprising at least the DSM 29870 as described above to improve the performance of an animal infected by *C. perfringens*. Within the meaning of the invention, "animal performance" may be determined by the body weight gain of the animal and/or by the feed conversion ratio and/or by the feed efficiency and/or by the digestibility of a nutrient in a feed (e.g. amino acid digestibility) and/or digestible energy or metabolizable energy in a feed and/or by nitrogen retention.

In a preferred embodiment of the invention "animal performance" is determined by the body weight gain of the animal and/or by the feed conversion ratio. By "improved animal performance" it is meant that there is increased body weight gain and/or reduced feed conversion ratio and/or improved digestibility of nutrients or energy in a feed and/or by improved nitrogen retention and/or increased feed efficiency resulting from the use of feed or feed premix of the present invention in feed in comparison to feed which does not comprise said feed or feed premix. Preferably, by "improved animal performance" it is meant that there is increased body weight gain and/or reduced feed conversion ratio.

In a preferred aspect of the invention, the animal feed or animal feed premix comprises at least the DSM 29870 bacterial strain described herein is used, wherein the bacterial count of the bacterial strains is between $1\times10^4$ and $1\times10^{14}$ CFU/kg of animal feed or feed premix, preferably between $1\times10^6$ and $1\times10^{12}$ CFU/kg of feed or feed premix, and more preferably between $1\times10^7$ and $1\times10^{11}$ CFU/kg of feed or feed premix. In a more preferred embodiment the bacterial count of the bacterial strains described herein is between $1\times10^8$ and $1\times10^{10}$ CFU/kg of feed or feed premix.

As used herein, the term "feed conversion ratio" refers to the amount of feed fed to an animal to increase the weight of the animal by a specified amount. Specifically FCR is the mass of the food eaten divided by the output, all over a specified period. FCR can be determined as described in the Examples. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition. In one embodiment the improvement of feed conversion rate (FCR) for Aspect 5, 6, 7 or 8 results in a FCR of −2.5% or less than −2.5%, such as less than −2.6%, such as less than −2.7%, such as less than −2.8%, such less than −2.9%, such as less than −3.0%. In a preferred embodiment the improvement of FCR results in a FCR of from −5% to −2% such as a FRC from −4% to −2%, such as s FCR of from −3.5% to −2.5%. In a specific embodiment the improvement of FCR for Aspect 1, 2, 3 or 4 results in a FCR within an interval selected from the group consisting of from −5% to −4.5%, from −4.5% to −4%, from −4% to −3.8%, from −3.8% to −3.6%, from −3.6% to −3.4%, from −3.4% to −3.2%, from −3.2 to −3.0%, from −3.0% to −2.8% and from −2.8 to −2.5%, or any combination of these intervals.

An "increased body weight gain" refers to an animal having increased body weight on being fed feed comprising a feed composition compared with an animal being fed a feed without said feed composition of the invention. Specifically, the Body Weight Gain of an animal is the increase of body weight of the animal over a specified time period. In one embodiment, the improvement in body weight gain if of at least 0.5% such at least 1%, such at least 2%, such at least 2,3%, such at least 3%, such at least 4%, such at least 5%, such at least 6%, such at least 6.5%, such at least 7%, such at least 8%, such at least 8%, such at least 10%. In one embodiment the improvement in body weight gain for Aspect 5, 6, 7 or 8 results in a body weight gain of at least 0.5%, such as at least 0.8%, such as at least 1.5%, such as at least 1.8%, such as at least 2.0%, such as at least 2.3%, such as at least %, such as at least 4.2%, such as at least 5.2%, such as at least 6.5%, such as at least 7.3%. In a preferred embodiment the improvement in body weight gain for Aspect 1, 2, 3 or 4 results in a body weight gain selected from the group consisting of from 1.8% to 2.0%, from 2.0% to 2.2%, from 2.2% to 2.4%, from 2.4% to 2.6%, from 2.6% to 2.8%, from 2.8% to 3.0%, from 3.0% to 3.2%, from 3.2% to 3.4%, from 3.4% to 3.6%, from 3.6% to 3.8%, from 3.8% to 4.0%, from 4% to 5%, from 5% to 7%, from 7% to 10%, or any combination thereof.

As used herein, the term "feed efficiency" refers to the amount of weight gain in an animal that occurs when the animal is fed ad-libitum or a specified amount of food during a period of time. By "increased feed efficiency" it is meant that the use of the feed or the feed premix according the present invention in feed results in an increased weight gain per unit of feed intake compared with an animal fed without said feed or feed premix being present.

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum. Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, mineral digestibility and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Nitrogen retention as used herein means a subject's ability to retain nitrogen from the diet as body mass. A negative nitrogen balance occurs when the excretion of nitrogen exceeds the daily intake and is often seen when the muscle is being lost. A positive nitrogen balance is often associated with muscle growth, particularly in growing animals. Nitrogen retention may be measured as the difference between the intake of nitrogen and the excreted nitrogen by means of the total collection of excreta and urine during a period of time. It is understood that excreted nitrogen includes undigested protein from the feed, endogenous proteinaceous secretions, microbial protein, and urinary nitrogen.

Method for Improving the Performance of an Animal Using *Bacillus* Strain DSM 29870

In another aspect the present invention relates to a method for improving the performance of an animal infected by *C. perfringens* comprising the step of administering to said animal a feed or feed premix comprising at least the *Bacillus* strain DSM 29870.

In a preferred aspect of the invention, the feed or feed premix comprises at least the DSMZ 29870 bacterial strain, wherein the bacterial count of each of the bacterial strains is between $1\times10^4$ and $1\times10^{14}$ CFU/kg of feed, preferably between $1\times10^6$ and $1\times10^{12}$ CFU/kg of feed, and more preferably between $1\times10^7$ and $1\times10^{11}$ CFU/kg of feed. In a more preferred embodiment the bacterial count of the bacterial strains described herein is between $1\times10^8$ and $1\times10^{10}$ CFU/kg of feed. Within the meaning of the invention, the terms "improving animal performance" are defined as above in the paragraph "use of the composition". In a specific embodiment, the invention deals with a method for improving the body weight gain and/or the feed conversion ratio of an animal infected by *C. perfringens* comprising the step of administering to said animal a feed composition comprising at least the *Bacillus* strain DSM 29870. As indicated above the animal is selected from the group consisting of swine and poultry. More specifically, the animal is selected from the group comprising chickens, broilers, layers, quails and turkey, domestic ducks or domestic geese or the young of pigeons, pigs, swine, piglets, growing pigs, or sows Method for Feeding an Animal Using *Bacillus* Strain DSM 29870

In another aspect the present invention relates to a method for feeding an animal infected by *C. perfringens* comprising administering a feed or feed premix comprising at least the *Bacillus* strain DSM29870 to said animal optionally in conjunction with other animal feed ingredients.

Within the meaning of the invention, the terms "improving animal performance" are defined as above. As indicated above the animal is selected from the group consisting of swine and poultry. More specifically, the animal is selected from the group comprising chickens, broilers, layers, quails and turkey, domestic ducks or domestic geese or the young of pigeons, pigs, swine, piglets, growing pigs, or sows. In a preferred aspect of the invention, the composition such as a feed comprises at least the DSMZ 29870 bacterial strain, wherein the bacterial count of each of the bacterial strains is between $1\times10^4$ and $1\times10^{14}$ CFU/kg of feed, preferably between $1\times10^6$ and $1\times10^{12}$ CFU/kg of feed, and more preferably between $1\times10^7$ and $1\times10^{11}$ CFU/kg of feed. In a more preferred embodiment the bacterial count of the bacterial strains described herein is between $1\times10^8$ and $1\times^{10}$ CFU/kg of feed. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

PREFERRED EMBODIMENTS

Preferred embodiments of the invention are described in the set of items herein below (cf. ITEM SET I, ITEM SET II and ITEM SET III).

Item Set I:
1. An animal feed or an animal feed additive comprising a *Bacillus* strain characterized in that:
   i) the *Bacillus* strain is non-hemolytic,
   ii) the *Bacillus* strain has antimicrobial activity against *Clostridium perfringens* and
   iii) the *Bacillus* strain improves body weight gain and/or feed conversion rate in chickens fed with the *Bacillus* strain.
2. An animal feed or an animal feed additive comprising a *Bacillus* strain characterized in that:
   i) the *Bacillus* strain is non-hemolytic,
   ii) the *Bacillus* strain has antimicrobial activity against *Clostridium perfringens* and
   iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.
3. An animal feed or an animal feed additive comprising a *Bacillus* strain characterized in that:
   i) the *Bacillus* strain is non-hemolytic,
   ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and
   iii) the *Bacillus* strain improves body weight gain and/or feed conversion rate in chickens fed with the *Bacillus* strain.
4. An animal feed or an animal feed additive comprising a *Bacillus* strain characterized in that:
   i) the *Bacillus* strain is non-hemolytic,
   ii) the *Bacillus* strain has antimicrobial activity against *Clostridium perfringens* and
   iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.
5. The animal feed or the animal feed additive according to any of items 1 to 3, wherein the *Bacillus* strain has enzymatic activity under aerobic and/or anaerobic conditions that hydrolyzes one or more of the substrates selected from the group consisting of Amylose, Arabinan, Arabinoxylan, Casein and Xylan.
6. The animal feed or the animal feed additive according to any of items 1 and 4, wherein the *Bacillus* strain improves one or more performance parameters in poultry selected from the list consisting of body weight gain, European Production Efficacy Factor and feed conversion rate in poultry fed with the *Bacillus* strain.
7. The animal feed or the animal feed additive according to item 3, wherein the *Bacillus* strain has antimicrobial activity against *Clostridium perfringens*.
8. The animal feed or the animal feed additive according to any of items 1 and 4, wherein the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.
9. The animal feed or the animal feed additive according to any of the previous items, wherein the *Bacillus* strain comprises 16S rDNA that is more than 98% sequence identity to SEQ ID NO: 1 and/or more than 98% sequence identity to SEQ ID NO: 2 and/or more than 98% sequence identity to SEQ ID NO: 3 and/or more than 98% sequence identity to SEQ ID NO: 4.
10. The animal feed or the animal feed additive according to any of the previous items, wherein the *Bacillus* strain is a *Bacillus subtilis* strain or a *Bacillus amyloliquefaciens* strain.
11. The animal feed or the animal feed additive according to any of the previous items, wherein the *Bacillus* strain has antimicrobial effect against *E. coli*.
12. The animal feed or the animal feed additive according to any of the previous items, wherein the *Bacillus* strain is the *Bacillus* strain having deposit accession number DSM 29869, or a strain having all of the identifying characteristics of *Bacillus* DSM 29869 or a mutant thereof that has antimicrobial activity against *Clostridium perfringens*.
13. The animal feed or the animal feed additive according to any of the previous items, wherein the *Bacillus* strain is the *Bacillus* strain having deposit accession number DSM 29870, or a strain having all of the identifying characteristics of *Bacillus* DSM 29870 or a mutant thereof that has antimicrobial activity against *Clostridium perfringens*.
14. The animal feed or the animal feed additive according to any of the previous items, wherein the *Bacillus* strain is the *Bacillus* strain having deposit accession number DSM 29871, or a strain having all of the identifying characteristics of *Bacillus* DSM 29871 or a mutant thereof that has antimicrobial activity against *Clostridium perfringens*.
15. The animal feed or the animal feed additive according to any of the previous items, wherein the *Bacillus* strain is the *Bacillus* strain having deposit accession number DSM 29872, or a strain having all of the identifying characteristics of *Bacillus* DSM 29872 or a mutant thereof that has antimicrobial activity against *Clostridium perfringens*.
16. The animal feed or the animal feed additive according to any of items 1 to 15, wherein the *Bacillus* spores of the animal feed or the animal feed additive are present as dried spores.
17. The animal feed or the animal feed additive according to any of items 1 to 16 which further comprises a carrier.

18. The animal feed or the animal feed additive according to item 17, wherein the carrier comprises one or more of the following compounds: water, glycerol, ethylene glycol, 1,2-propylene glycol or 1,3-propylene glycol, sodium chloride, sodium benzoate, potassium sorbate, sodium sulfate, potassium sulfate; magnesium sulfate, sodium thiosulfate, calcium carbonate, sodium citrate, dextrin, maltodextrin, glucose, sucrose, sorbitol, lactose, wheat flour, wheat bran, corn gluten meal, starch and cellulose.

19. The animal feed or the animal feed additive according to any of items 1 to 18, wherein the animal feed or animal feed additive comprises from $10^5$ to $10^{12}$ CFU/g of isolated Bacillus spores.

20. The animal feed or animal feed additive of any of items 1 to 19, wherein at least 70% (such as at least 80% or at least 90%) of the Bacillus spores survive gastric stability in a mono-gastric animal such as chickens.

21. The animal feed or animal feed additive according to any of items 1 to 20 which further comprises one or more components selected from the list consisting of:
one or more enzymes;
one or more additional microbes;
one or more vitamins;
one or more minerals;
one or more amino acids; and one or more other feed ingredients.

22. The animal feed or animal feed additive according to any of items 1 to 21, wherein the bacterial count of each Bacillus spore is $1 \times 10^4$ and $1 \times 10^{14}$ CFU/kg of animal feed or animal feed additive, preferably between $1 \times 10^6$ and $1 \times 10^{12}$ CFU/kg of animal feed or animal feed additive, and more preferably between $1 \times 10^7$ and $1 \times 10^{11}$ CFU/kg of animal feed or animal feed additive.

23. The animal feed or animal feed additive according to any of items 1 to 22, wherein the animal feed or animal feed additive is a mono-gastric animal feed or animal feed additive.

24. The animal feed or animal feed additive according to any of items 1 to 23, wherein the Bacillus strain improves gut health of chickens with infection of Clostridium perfringens by having antimicrobial activity against Clostridium perfringens.

25. The mono-gastric animal feed or animal feed additive according to item 24, wherein the mono-gastric animal is selected from the group consisting of pigs, swine, piglets, sows, poultry, turkeys, ducks, chicken, broilers, layers, chicks, fish and crustaceans.

26. An animal feed or animal feed additive according to any of items 1 to 25 for the treatment of necrotic enteritis or the treatment of a Clostridium perfringens infection.

27. The animal feed or animal feed additive according to item 26 for treatment of mono-gastric animals.

28. A method of treating a Clostridium perfringens infection or for treating necrotic enteritis in an animal comprising administrating the animal feed or the animal feed additive according to any of items 1 to 27 to the animal.

29. Use of the animal feed or the animal feed additive according to any of items 1 to 27 to treat a Clostridium perfringens infection or for treating necrotic enteritis in an animal.

30. Use of the animal feed or the animal feed additive according to any of items 1 to 27 to improve one or more performance parameters of an animal selected from the group consisting of: improving the feed conversion ratio, improving the body weight gain, improving the European Production Efficacy Factor, improving the feed efficiency and improving the health.

31. A method of improving one or more performance parameters of an animal selected from the group consisting of: improving the feed conversion ratio, improving the body weight gain, improving the European Production Efficacy Factor, improving the feed efficiency and improving the health, comprising administering the animal feed or animal feed additive according to any of items 1 to 27 to the animal.

Item Set II:

1. Use of an animal feed or an animal feed premix comprising at least the Bacillus strain DSM 29870 for improving the performance of an animal.

2. The use of the animal feed or the animal feed premix comprising at least the Bacillus strain DSM 29870 according to item 1 for improving the feed conversion ratio and/or for improving the body weight gain and/or for improving the feed efficiency, and/or the weight, and/or the feed intake.

3. The use of the animal feed or the animal feed premix comprising at least the Bacillus strain DSM 29870 according to item 1 or 2 wherein the animal is selected from the group consisting of poultry and swine.

4. The use of the animal feed or the animal feed premix comprising at least the Bacillus strain DSM 29870 according to item 3 wherein the animal is selected from chickens, broilers, layers, quails and turkey, domestic ducks or domestic geese or the young of pigeons, pigs, swine, piglets, growing pigs, or sows.

5. Use of the animal feed or the animal feed additive according to anyone of items 1 to 4 wherein the composition is a feed composition such an animal feed or a premix.

6. Use of the animal feed according to any of item 1 to 4 wherein the feed comprises at least the DSM 29870 Bacillus strain and wherein the bacterial count of each bacterial strain is between $1 \times 10^4$ and $1 \times 10^{14}$ CFU/kg of animal feed, preferably between $1 \times 10^6$ and $1 \times 10^{12}$ CFU/kg of animal feed, and more preferably between $1 \times 10^7$ and $1 \times 10^{11}$ CFU/kg of animal feed and even more preferably between $1 \times 10^8$ and $1 \times 10^{10}$ CFU/kg of animal feed.

7. A method for improving the performance of an animal comprising administering to said animal an animal feed or an animal feed premix comprising at least the Bacillus strain DSM29870.

8. The method for improving the performance of an animal according to item 7 such as improving the feed conversion ratio and/or improving the body weight gain and/or improving the feed efficiency, and/or the weight, and/or improving feed intake.

9. The method for improving the performance of an animal according to item 7 or 8 wherein the animal is selected from the group consisting of poultry and swine.

10. The method for improving the performance of an animal according to item 9 wherein the animal is selected from the group comprising chickens, broilers, layers, quails and turkey, domestic ducks or domestic geese or the young of pigeons, pigs, swine, piglets, growing pigs, or sows.

11. A method for improving the performance of an animal according to anyone of the items 7 to 10 wherein the bacterial count of each bacterial strain is between $1 \times 10^4$ and $1 \times 10^{14}$ CFU/kg of animal feed, preferably between $1 \times 10^6$ and $1 \times 10^{12}$ CFU/kg of animal feed, and more preferably between $1 \times 10^7$ and $1 \times 10^{11}$ CFU/kg of animal feed and even more preferably between $1 \times 10^8$ and $1 \times 10^{10}$ CFU/kg of animal feed.

12. A method for feeding an animal comprising administering an animal feed or an animal feed premix comprising at least the Bacillus strain DSM 29870 to said animal optionally in conjunction with other animal feed ingredients.

13. The method for feeding an animal according to item 12 wherein the animal is selected from the group consisting of poultry and swine.

14. The method for feeding an animal according to item 13 wherein the animal is selected from the group comprising chickens, broilers, layers, quails and turkey, domestic ducks or domestic geese or the young of pigeons, pigs, swine, piglets, growing pigs, or sows.

15. A method for feeding an animal according to anyone of items 12 to 14 wherein the bacterial count of each bacterial strain is between $1\times10^4$ and $1\times10^{14}$ CFU/kg of animal feed, preferably between $1\times10^6$ and $1\times10^{12}$ CFU/kg of animal feed, and more preferably between $1\times10^7$ and $1\times10^{11}$ CFU/kg of animal feed and even more preferably between $1\times10^8$ and $1\times10^{10}$ CFU/kg of animal feed.

16. A feed or a feed premix for improving the performance of poultries and swine comprising at least the *Bacillus* strain DSM 29870.

17. The feed or feed premix according to item 16 further comprising one or more enzymes; one or more additional microbes; one or more vitamins; one or more minerals; one or more amino acids; and one or more other feed or feed premix ingredients.

18. The feed according to item 16 or 17 wherein the bacterial count of each bacterial strain is between $1\times10^4$ and $1\times10^{14}$ CFU/kg of animal feed, preferably between $1\times10^6$ and $1\times10^{12}$ CFU/kg of animal feed, and more preferably between $1\times10^7$ and $1\times10^{11}$ CFU/kg of animal feed and even more preferably between $1\times10^8$ and $1\times10^{10}$ CFU/kg of animal feed.

Item Set III:

1. An animal feed or an animal feed additive comprising a *Bacillus* strain characterized in that:
    i) the *Bacillus* strain is non-hemolytic,
    ii) the *Bacillus* strain has antimicrobial activity against *Clostridium perfringens* and
    iii) the *Bacillus* strain improves body weight gain and/or feed conversion rate in chickens fed with the *Bacillus* strain.

2. An animal feed or an animal feed additive comprising a *Bacillus* strain characterized in that:
    i) the *Bacillus* strain is non-hemolytic,
    ii) the *Bacillus* strain has antimicrobial activity against *Clostridium perfringens* and
    iii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline.

3. An animal feed or an animal feed additive comprising a *Bacillus* strain characterized in that:
    i) the *Bacillus* strain is non-hemolytic,
    ii) the *Bacillus* strain is sensitive to at least seven such as eight of the antibiotics selected from the group consisting of Vancomycin, Clindamycin, Chloramphenicol, Gentamicin, Kanamycin, Streptomycin, Erythromycin and Tetracycline and
    iii) the *Bacillus* strain improves body weight gain and/or feed conversion rate in chickens fed with the *Bacillus* strain.

4. An animal feed or an animal feed additive comprising a *Bacillus* strain characterized in that:
    i) the *Bacillus* strain is non-hemolytic,
    ii) the *Bacillus* strain has antimicrobial activity against *Clostridium perfringens* and
    iii) the *Bacillus* strain has enzymatic activity under aerobic and/or anaerobic conditions that hydrolyzes one or more of the substrates selected from the group consisting of Amylose, Arabinan, Arabinoxylan, Casein and Xylan.

5. The animal feed or the animal feed additive according to any of the previous items, wherein the *Bacillus* strain comprises 16S rDNA that is more than 98% sequence identity to SEQ ID NO: 1 and/or more than 98% sequence identity to SEQ ID NO: 2 and/or more than 98% sequence identity to SEQ ID NO: 3 and/or more than 98% sequence identity to SEQ ID NO: 4.

6. The animal feed or the animal feed additive according to any of the previous items, wherein the *Bacillus* strain is a *Bacillus subtilis* strain or a *Bacillus amyloliquefaciens* strain.

7. The animal feed or the animal feed additive according to any of the previous items, wherein the *Bacillus* strain has antimicrobial effect against *E. coli*.

8. The animal feed or the animal feed additive according to any of the previous items, wherein the *Bacillus* strain is the *Bacillus* strain having deposit accession number DSM 29869, or a strain having all of the identifying characteristics of *Bacillus* DSM 29869 or a mutant thereof that has antimicrobial activity against *Clostridium perfringens*.

9. The animal feed or the animal feed additive according to any of the previous items, wherein the *Bacillus* strain is the *Bacillus* strain having deposit accession number DSM 29870, or a strain having all of the identifying characteristics of *Bacillus* DSM 29870 or a mutant thereof that has antimicrobial activity against *Clostridium perfringens*.

10. The animal feed or the animal feed additive according to any of the previous items, wherein the *Bacillus* strain is the *Bacillus* strain having deposit accession number DSM 29871, or a strain having all of the identifying characteristics of *Bacillus* DSM 29871 or a mutant thereof that has antimicrobial activity against *Clostridium perfringens*.

11. The animal feed or the animal feed additive according to any of the previous items, wherein the *Bacillus* strain is the *Bacillus* strain having deposit accession number DSM 29872, or a strain having all of the identifying characteristics of *Bacillus* DSM 29872 or a mutant thereof that has antimicrobial activity against *Clostridium perfringens*.

12. The animal feed or the animal feed additive according to any of item 1 to 11, wherein the *Bacillus* spores of the animal feed or the animal feed additive are present as dried spores.

13. The animal feed or the animal feed additive according to any of items 1 to 12 which further comprises a carrier.

14. The animal feed or the animal feed additive according to item 13, wherein the carrier comprises one or more of the following compounds: water, glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch and cellulose.

15. The animal feed or the animal feed additive according to any of items 1 to 14, wherein the animal feed or animal feed additive comprises from 105 to $10^{12}$ CFU/g of isolated *Bacillus* spores.

16. The animal feed or animal feed additive according to any of items 1 to 15, wherein the bacterial count of each *Bacillus* spore is $1\times10^4$ and $1\times10^{14}$ CFU/kg of animal feed or animal feed additive, preferably between $1\times10^6$ and $1\times10^{12}$ CFU/kg of animal feed or animal feed additive, and more preferably between $1\times10^7$ and $1\times10^{11}$ CFU/kg of animal feed or animal feed additive.

17. The animal feed or animal feed additive according to any of items 1 to 16, wherein the *Bacillus* strain improves gut health of chickens with infection of *Clostridium perfringens* by having antimicrobial activity against *Clostridium perfringens*.

18. The mono-gastric animal feed or animal feed additive according to item 17, wherein the mono-gastric animal is selected from the group consisting of pigs, swine, piglets, sows, poultry, turkeys, ducks, chicken, broilers, layers, chicks, fish and crustaceans.

19. An animal feed or animal feed additive according to any of items 1 to 18 for the treatment of necrotic enteritis or the treatment of a *Clostridium perfringens* infection.

20. A method of treating a *Clostridium perfringens* infection or for treating necrotic enteritis in an animal comprising administrating the animal feed or the animal feed additive according to any of items 1 to 19 to the animal.

21. Use of the animal feed or the animal feed additive according to any of items 1 to 19 to treat a *Clostridium perfringens* infection or for treating necrotic enteritis in an animal.

22. Use of the animal feed or the animal feed additive according to any of items 1 to 19 to improve one or more performance parameters of an animal selected from the group consisting of: improving the feed conversion ratio, improving the body weight gain, improving the European Production Efficacy Factor, improving the feed efficiency and improving the health.

23. A method of improving one or more performance parameters of an animal selected from the group consisting of: improving the feed conversion ratio, improving the body weight gain, improving the European Production Efficacy Factor, improving the feed efficiency and improving the health, comprising administering the animal feed or animal feed additive according to any of items 1 to 19 to the animal.

24. Use of an animal feed or an animal feed premix comprising at least the *Bacillus* strain DSM 29870 for improving the performance of an animal.

25. The use of the animal feed or the animal feed premix comprising at least the *Bacillus* strain DSM29870 according to item 24 for improving the feed conversion ratio and/or for improving the body weight gain and/or for improving the feed efficiency, and/or the weight, and/or the feed intake.

26. The use of the animal feed or the animal feed premix comprising at least the *Bacillus* strain DSM29870 according to item 24 or 25 wherein the animal is selected from the group consisting of poultry and swine.

27. The use of the animal feed or the animal feed premix comprising at least the *Bacillus* strain DSM29870 according to item 26 wherein the animal is selected from chickens, broilers, layers, quails and turkey, domestic ducks or domestic geese or the young of pigeons, pigs, swine, piglets, growing pigs, or sows.

28. Use of the animal feed according to anyone or items 24 to 27 wherein the feed comprises at least the DSM 29870 *Bacillus* strain and wherein the bacterial count of each bacterial strain is between $1\times10^4$ and $1\times10^{14}$ CFU/kg of animal feed, preferably between $1\times10^6$ and $1\times10^{12}$ CFU/kg of animal feed, and more preferably between $1\times10^7$ and $1\times10^{11}$ CFU/kg of animal feed and even more preferably between $1\times10^8$ and $1\times^{10}10$ CFU/kg of animal feed.

29. A method for improving the performance of an animal comprising administering to said animal an animal feed or an animal feed premix comprising at least the *Bacillus* strain DSM29870.

30. The method for improving the performance of an animal according to item 29 such as improving the feed conversion ratio and/or improving the body weight gain and/or improving the feed efficiency, and/or the weight, and/or improving feed intake.

31. The method for improving the performance of an animal according to item 29 or 30 wherein the animal is selected from the group consisting of poultry and swine.

32. The method for improving the performance of an animal according to item 31 wherein the animal is selected from the group comprising chickens, broilers, layers, quails and turkey, domestic ducks or domestic geese or the young of pigeons, pigs, swine, piglets, growing pigs, or sows.

33. A method for improving the performance of an animal according to anyone of the items 29 to 32 wherein the bacterial count of each bacterial strain is between $1\times10^4$ and $1\times10^{14}$ CFU/kg of animal feed, preferably between $1\times10^6$ and $1\times10^{12}$ CFU/kg of animal feed, and more preferably between $1\times10^7$ and $1\times10^{11}$ CFU/kg of animal feed and even more preferably between $1\times10^8$ and $1\times^{10}10$ CFU/kg of animal feed.

34. A method for feeding an animal comprising administering an animal feed or an animal feed premix comprising at least the *Bacillus* strain DSM 29870 to said animal optionally in conjunction with other animal feed ingredients.

35. The method for feeding an animal according to item 34 wherein the animal is selected from the group consisting of poultry and swine.

36. The method for feeding an animal according to item 35 wherein the animal is selected from the group comprising chickens, broilers, layers, quails and turkey, domestic ducks or domestic geese or the young of pigeons, pigs, swine, piglets, growing pigs, or sows.

37. A method for feeding an animal according to item 34 or 35 wherein the bacterial count of each bacterial strain is between $1\times10^4$ and $1\times10^{14}$ CFU/kg of animal feed, preferably between $1\times10^6$ and $1\times10^{12}$ CFU/kg of animal feed, and more preferably between $1\times10^7$ and $1\times10^{11}$ CFU/kg of animal feed and even more preferably between $1\times10^8$ and $1\times10^{10}$ CFU/kg of animal feed.

38. A feed or a feed premix for improving the performance of poultries and swine comprising at least the *Bacillus* strain DSM29870.

39. The feed or feed premix according to item 38 further comprising one or more enzymes; one or more additional microbes; one or more vitamins; one or more minerals; one or more amino acids; and one or more other feed or feed premix ingredients.

40. The feed according to item 38 or 39 wherein the bacterial count of each bacterial strain is between $1\times10^4$ and $1\times10^{14}$ CFU/kg of animal feed, preferably between $1\times10^6$ and $1\times10^{12}$ CFU/kg of animal feed, and more preferably between $1\times10^7$ and $1\times10^{11}$ CFU/kg of animal feed and even more preferably between $1\times10^8$ and $1\times10^{10}$ CFU/kg of animal feed.

EXAMPLES

Example 1: Screening for Hemolysis Negative *Bacillus* Strains

Hemolysis was tested according to the Technical Guidance on the assessment of the toxigenic potential of *Bacillus* species used in animal nutrition, EFSA Journal 2011; 9(11): 2445.

Sheep blood agar plates were purchased as ready to use (Becton Dickenson art 254053 or 254087). Alternatively, the agar plates can be prepared by adding 5% defibrinated sheep blood (obtained from Statens Serum Institute, Denmark) to TS-agar (Oxoid CM 131). Agar should be autoclaved at 121° C. for 20 minutes and cooled down to about 40° C. before adding the blood immediately before pouring the plates.

The Bacillus strains were taken from the preservation at −80° C. and streaked on TS-agar plate, which was incubated at 30° C. overnight or until growth appeared. From a single colony as little as possible of the material was used to streak a line on ¼ of an agar plate. The plate was incubated at 30° C. for 72 hours. Hemolysis/clearing zones of the Bacillus strains to be tested were compared with the positive and negative control. As positive control Bacillus subtilis ATCC21332 was used. As negative control Bacillus subtilis 168, (BGSC-1A1, Bacillus Genetic Stock Center) was used.

In a screening of 599 independent isolates of Bacillus 223 strains (37%) were hemolysis negative. In another screening 21 of 65 independent isolates of Bacillus (32%) were hemolysis negative. Both screenings exclusively comprised strains that based on identification by 16S rDNA sequencing belong to Bacillus subtilis, Bacillus licheniformis, Bacillus pumilus or Bacillus amyloliquefaciens or close relatives to these four species.

The non-Hemolytic Bacillus strains therefore seem to be common and fairly abundant in nature, but only comprising a minority of the natural strains. The non-hemolytic strains seem to be more abundant in Bacillus licheniformis, while most Bacillus amyloliquefaciens strains appear hemolytic. All the non-hemolytic strains were tested for inhibition of growth of Clostridium perfringens. The following strains from screening were all hemolysis negative and among those selected for further studies: DSM 29869, DSM 29870, DSM 29871 and DSM 29872. Clostat (Bacillus PB6) was determined to be hemolytic.

Example 2: Determination of Inhibition of Growth of Clostridium perfringens

All the non-hemolytic strains were tested for inhibition of growth of Clostridium perfringens strains 23 and 48 (both are netB positive) [Gholamiandekhordi A R, Ducatelle R, Heyndrickx M, Haesebrouck F, Van Immerseel F. 2006. Molecular and phenotypical characterization of *Clostridium perfringens* isolates from poultry flocks with different dis-easestatus. Vet. Microbiol. 113:143-152], were grown overnight in tryptic soy broth (BD part 211822) supplemented with 0.6% yeast extract (BD part 212750) at 35° C. under static anaerobic conditions. 250 μL of the overnight culture of *Clostridium perfringens* was added to 250 mL of tryptic soy agar supplemented with 0.6% yeast extract at 40° C. and poured into rectangular petri plates (Nunc part 267060). The inoculated agar was allowed to cool at room temperature after which an 8 mm diameter well was made in the agar. Plates were stored in absence of oxygen until use.

The *Bacillus* strain DSM 29869, DSM 29870, DSM 29871, or DSM 29872 was grown overnight in tryptic soy broth at 35° C. under aerobic conditions. 1000 μL of *Bacillus* culture was collected and fractionated into cell-free supernatant and cells by centrifugation. 20 μL of cell-free supernatant or 100× diluted cells in phosphate buffered saline were added directly to the wells in the *Clostridium perfringens* inoculated agar plates. A control well contained 20 μL of phosphate buffer saline. The plates were incubated for 18 hours at 35° C. under anaerobic conditions.

Inhibition of the *Clostridium perfringens* strain was noted by a circular clearing zone around the well of interest. The phosphate buffer saline well was considered a negative control based on lack of clearing zone around the well.

Cell-free supernatant and 100× diluted cells of *Bacillus* strains DSM 29869, DSM 29870, DSM 29871, and DSM 29872 were able to consistently inhibit growth of *C. perfringens* strains 23 and 48 in vitro. Inhibition was also seen by competitor strain "CloSTAT", for both supernatant and cells, but was not seen with competitor strain GalliproTect. "CloSTAT" is a strain of *Bacillus amyloliquefaciens* that was isolated from the commercial DFM product CloSTAT, Kemin. "GalliproTect" is a strain of *Bacillus licheniformis* that was isolated from the commercial product Gallipro Tect, Chr Hansen.

Example 3: Identification, Characterization and Deposit of the Biological Material The following biological materials were deposited under the terms of the Budapest Treaty at Leibniz-Institut DSMZ-Deutsche Sammlung von Mikro-organismen und Zellkulturen GmbH, Inhoffenstraβe 7 B, 38124 Braunschweig Germany, and given the following accession numbers:

TABLE 3.1

Deposit of Biological Material

| Identification | Accession Number | Date of Deposit |
|---|---|---|
| *Bacillus amyloliquefaciens* | DSM 29869 | Jan. 12, 2015 |
| *Bacillus subtilis* | DSM 29870 | Jan. 12, 2015 |
| *Bacillus subtilis* | DSM 29871 | Jan. 12, 2015 |
| *Bacillus amyloliquefaciens* | DSM 29872 | Jan. 12, 2015 |

The strains have been deposited under conditions that assure that access to the culture will be available during the pendency of this patent application to one determined by foreign patent laws to be entitled thereto. The deposits represent a substantially pure culture of the deposited strain. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Sequencing of 16S rDNA Genes

DNA was extracted from a culture of DSM 29869, DSM 29870, DSM 29871 and DSM 29872 using QiaAmp DNA Blood Mini Kit (Qiagen art 51106). The kit was used as recommended for extraction of DNA from gram positive bacteria.

16S rDNA was amplified in a total volume of 50 μl by mixing: 10 pmol of each of Primer 16S F and 16S R, 0.2 mM of each nucleotide, 2.5 units Ampli taq, 1× Ampli taq buffer, 5 μl DNA template and by using the following PCR program: 94° C. 2 min (94° C. 30 s, 52° C. 30 S, 72° C. 1 min)×35, 72° C. 10 min on a Perkin Elmer PCR machine. The PCR product was sequenced by Novozymes DNA sequencing facility using primer 530R, 357F, 1390R and 1100F.

TABLE 3.2

Primers:

| Primer | Sequence | SEQ ID NO |
|---|---|---|
| 16S-F | 5'-GAGTTTGATCCTGGCTCAG-3' | SEQ ID NO: 8 |
| 16S-R | 5'-AGAAAGGAGGTGATCCAGCC-3' | SEQ ID NO: 9 |

TABLE 3.2 -continued

```
Primers:
Primer Sequence                         SEQ ID NO

794-R  5'-ATCTAATCCTGTTTGCTCCCC-3'     SEQ ID NO: 10

357-F  5'-TACGGGAGGCAGCAG-3'           SEQ ID NO: 11

1390-R  5'-CGGTGTGTRCAAGGCCC-3'         SEQ ID NO: 12

1000-F  5'-CAACGAGCGCAACCCT',           SEQ ID NO: 13
```

Degeneration of primer 1390-R: R is A or G. The 16 S rDNA sequences from DSM 29869, DSM 29870, DSM 29871 and DSM 29872 are shown as SEQ ID NO: 1-4 in the sequence listing respectively. The 16 S rDNA sequences from DSM 29869, DSM 29870, DSM 29871 and DSM 29872 were analyzed by BLAST against EMBL database and showed identity to 16 S rDNA sequences of *Bacillus subtilis* (SEQ ID NO: 2 and SEQ ID NO: 3) and to *Bacillus amyloliquefaciens* (SEQ ID NO: 1 and SEQ ID NO: 4).

In order to study the phylogenetic affiliation of SEQ ID NO: 1 to SEQ ID NO: 4 the sequences were analyzed by a ClustalW alignment in MegAlign (DNASTAR) using SEQ ID NO: 5 to SEQ ID NO: 7 as benchmark. These sequences are reference 16S rDNA sequences of the type strains of *Bacillus vallismortis* taken from AB021198 (SEQ ID NO: 5), *Bacillus subtilis* taken from AJ276351 (SEQ ID NO: 6) and *Bacillus amyloliquefaciens* taken from AB255669 (SEQ ID NO: 7).

The ClustalW alignment of SEQ ID NO: 1 to SEQ ID NO: 7 (FIG. 1) shows 7 nucleotide positions where 2 or more sequences have a nucleotide that deviates from the other. For numbering the positions in SEQ ID NO: 6 are used. At position 152 SEQ ID NO: 2 is identical to *Bacillus amyloliquefaciens* and *Bacillus vallismortis*, but different from the rest that are identical to each other. At position 174 SEQ ID NO: 1 and SEQ ID NO: 4 are identical to *Bacillus amyloliquefaciens*, but different from the rest that are identical to each other. At position 257 SEQ ID NO: 4 is identical to *Bacillus amyloliquefaciens*, but different from the rest that are identical to each other. At position 437, 444 and 455 SEQ ID NO: 2 and SEQ ID NO: 3 are identical to *Bacillus subtilis*, but different from the rest that are identical to each other. At position 1223 SEQ ID NO: 1 is identical to *Bacillus amyloliquefaciens*, but different from the rest that are identical to each other. The variation in the 16S rDNA genes support the species affiliation seen in the BLAST report.

Description of the Biological Material

*Bacillus amyloliquefaciens* DSM 29869 was isolated by Novozymes (Novo Nordisk) from an environmental sample collected at Jamaica in 1990. The strain was identified as *Bacillus amyloliquefaciens* based on 16S rDNA sequencing

*Bacillus subtilis* DSM 29870 was isolated by Novozymes (Novo Nordisk) from an environmental sample collected at Jamaica in 1990. The strain was identified as *Bacillus subtilis* based on 16S rDNA sequencing.

*Bacillus subtilis* DSM 29871 was isolated for Novozymes by a Danish high-school student at Brønderslev Gymnasium from a soil sample from private property in Denmark in 2008. The strain was identified as *Bacillus subtilis* based on 16S rDNA sequencing.

*Bacillus amyloliquefaciens* DSM 29872 was isolated from an environmental sample from the USA in 2008. The strain was identified as *Bacillus amyloliquefaciens* based on 16S rDNA sequencing.

Example 4: Determination of Inhibition of Growth of *Escherichia coli*

*Escherichia coli* strains, ATCC10536 or ATCC25922, were grown overnight in tryptic soy broth (BD part 211822) supplemented with 0.6% yeast extract (BD part 212750) at 35° C. under static anaerobic conditions. 100 µL of the overnight culture of *Escherichia coli* was added to 250 mL of tryptic soy agar supplemented with 0.6% yeast extract at 40° C. and poured into rectangular petri plates (Nunc part 267060). The inoculated agar was then allowed to cool at room temperature after which an 8 mm diameter well was made in the agar.

The *Bacillus* strain DSM 29869, DSM 29870, DSM 29871, or DSM 29872 was grown overnight in tryptic soy broth at 35° C. under aerobic conditions. 1000 µL of *Bacillus subtilis* culture was collected and fractionated into cell-free supernatant and cells by centrifugation. 20 µL of cell-free supernatant or 100× diluted cells in phosphate buffer saline were added directly to the wells in the *Escherichia coli* inoculated agar plates. A control well contained 20 µL of phosphate buffer saline. The plates were incubated for 18 hours at 30° C. under aerobic conditions.

Inhibition of the *Escherichia coli* strain was noted by a circular clearing zone around the well of interest. The phosphate buffer saline well was considered a negative control based on lack of clearing zone around the well.

Cell-free supernatant and 100× diluted cells of *Bacillus* strains DSM 29869, DSM 29870, DSM 29871, and DSM 29872 were able to consistently inhibit growth of the *E. coli* strains ATCC10535 and ATCC25922 in vitro. Inhibition was also seen by competitor strain CloSTAT, for both supernatant and cells.

Example 5: Sensitivity to Antibiotics

The minimal inhibitory concentrations (MIC) of eight antibiotics against *Bacillus* strains DSM 29869, DSM 29870, DSM 29871, and DSM 29872 were determined using broth micro dilution essentially as described in the CLSI guidelines (M07-A9 Methods for Dilution Antimicrobial Susceptibility Tests for Bacteria That Grow Aerobically; 2012). Only modification was that volumes were changed; 90 µl Mueller Hinton Broth 2 with bacteria was added to 10 µl antibiotics dilutions, cfu's of bacteria and concentration of antibiotics were changed so final concentrations and final cfu's matched the guideline. The plates were incubated for 20-24 h instead of 16-20 h. The control strain recommended in the CLSI standard *Staphylococcus aureus* ATCC 29213 was used as control strain.

Strains:
*Bacillus amyloliquefaciens* DSM 29869
*Bacillus subtilis* DSM 29870
*Bacillus subtilis* DSM 29871
*Bacillus amyloliquefaciens* DSM 29872
*S. aureus* ATCC 29213

Antibiotics:
Chloramphenicol (Sigma C1919, 10 mg/ml, solubilized in 96% ethanol)
Clindamycin (Sigma PHR1159, 10 mg/ml, solubilized in water)
Erythromycin (ABBOTICIN from Amdipharm 40501, 50 mg/ml, solubilized in 96% ethanol)
Gentamycin (Biomedicals inc., 190057, 10 mg/ml, solubilized in water)
Kanamycin (Sigma, CAS no. 25389-94-0, 50 mg/ml, solubilized in water)

Streptomycin (Sigma, S1277, 10 mg/ml, solubilized in water)
Tetracycline (Sigma, T3383, 10 mg/ml, solubilized in water)
Vancomycin (Sigma, V-8138, 10 mg/ml, solubilized in water)
Mueller Hinton Broth 2 (Sigma/Fluka 90922)
0.9% NaCl (Sigma/RdH 31434/Merck 106404)
Tryptone soya agar plates (Oxoid CM 131)
Microtiter plates: Costar plate, polypropylene, round bottom, Corning 3879
Preparation of Bacteria:

A few colonies of *Bacillus* spp. (<1 day old) were inoculated into Mueller Hinton Broth 2 (MHB) and incubated for around 4 hours at 37° C. $OD_{600}$ (BioPhotometer plus, Eppendorf) was measured and adjusted to 0.25 (equivalent to McFarland 0.5) in MHB. For the control strain direct colony suspension was used. A few colonies of *S. aureus* ATCC 29213 (<1 day old) were suspended in MHB and $OD_{600}$ (BioPhotometer plus, Eppendorf) was measured and adjusted to 0.10-0.12 (equivalent to McFarland 0.5) in MHB. The bacterial suspensions were diluted 200× in MHB.
Preparation of Assay Plates:

Antibiotics were diluted to the concentration of 640 µg/mL in MHB. A two fold dilution series was prepared in MHB down to the concentration 0.625 µg/ml. 10 µl of each dilution and of each antibiotic was pipetted into a micro-titre plate. Later, when the antibiotics were mixed with the suspension of bacteria, the samples were diluted 10× (10 µL sample in a total volume of 100 µl). This resulted in the final test range of 0.06-64 µg/ml.

If the plates were not used right away the plates were stored in the freezer at −20° C. until usage.

90 µl of the bacterial suspensions were added to the assay plates. The assay plates were incubated in a plastic bag with at wet cloth at 37° C. for 20-24 h. The MIC was determined as the lowest concentration of antibiotic that completely inhibited growth of bacteria as detected by the unaided eye.
CFU Estimation:

A 10-fold dilution series in 0.9% NaCl was made to the $10^{-3}$ of the cultures inoculated into the micro-titre plate. 2×100 ul from the $10^{-3}$ dilution were plated onto two TSA plates. The plates were incubated overnight at 37° C. Number of CFU/ml was counted.

Three biological replicates of the assay were performed for *Bacillus subtilis* DSM 29871, *Bacillus amyloliquefaciens* DSM 29869 and *Bacillus subtilis* DSM 29870 (MIC 1-3), while four biological replicates were performed for *Bacillus amyloliquefaciens* DSM 29872 (MIC 2-5).
Results:

The MIC values obtained for *B. subtilis* DSM 29870 showed that the breakpoint values were equal to or below the breakpoint values given in the EFSA guideline (EFSA journal 2012; 10(6):2740). For *B. subtilis* DSM 29869 the MIC values obtained in two out of the three biological replicates showed MIC values equal to or below the breakpoint. In MIC 1 the value for Tetracycline was 16. However, due to analytical variance of the method MIC results of one dilution above the breakpoint is in general accepted and the strain may be regarded as being sensitive. Thus, according to EFSA these two strains are regarded as sensitive to all the 8 antibiotics included in the test (Table 5.2 and 5.3).

For the strains *B. subtilis* DSM 29871 and *B. amyloliquefaciens* DSM 29872 the MIC values showed that the two strains were sensitive to seven out of the eight antibiotics (Table 5.1 and 5.4). An increased tolerance was observed towards Streptomycin and according to EFSA the strains are classified as resistant to Streptomycin.

As a control *S. aureus* ATCC 29213 was tested in parallel and had MIC values within the ranges given by the CLSI standard (M100-S24 Performance Standards for Antimicrobial Susceptibility Testing; informational Supplement, 2014) (Table 5.5).

The amount of bacteria inoculated into the assay plates was measured (CFU/ml). In general the CFU/ml was very close to the target value of 5*105 CFU/ml. However, the CFU/ml for *Bacillus* strains may be associated with some uncertainty, since the bacteria tend to aggregate and once aggregated will only result in one colony forming unit (Table 5.1 and 5.2).

TABLE 5.1

MIC results for *B. subtilis* DSM 29871

| Antibiotic | MIC 1 µg/ml | MIC 2 µg/ml | MIC 3 µg/ml | EFSA* breakpoints µg/ml |
|---|---|---|---|---|
| Chloramphenicol | 8 | 4 | 8 | 8 |
| Clindamycin | 0.5 | 0.25 | 0.5 | 4 |
| Erythromycin | 0.125 | 0.125 | 0.125 | 4 |
| Gentamycin | 0.25 | 0.125 | 0.25 | 4 |
| Kanamycin | 2 | 1 | 2 | 8 |
| Streptomycin | 32 | 16 | 32 | 8 |
| Tetracycline | 2 | 4 | 4 | 8 |
| Vancomycin | 0.25 | 0.25 | 0.25 | 4 |
| CFU/ml | 3.6*$10^5$ | n.r. | n.r. | |

*EFSA Journal 2012; 10(6): 2740 n.r. not registered

TABLE 5.2

MIC results for *B. amyloliquefaciens* DSM 29869

| Antibiotic | MIC 1 µg/ml | MIC 2 µg/ml | MIC 3 µg/ml | EFSA* breakpoints µg/ml |
|---|---|---|---|---|
| Chloramphenicol | 4 | 4 | 4 | 8 |
| Clindamycin | 1 | 0.5 | 1 | 4 |
| Erythromycin | 0.5 | 0.06 | 0.06 | 4 |
| Gentamycin | 0.5 | 0.125 | 0.06 | 4 |
| Kanamycin | 2 | 0.5 | 0.5 | 8 |
| Streptomycin | 2 | 4 | 4 | 8 |
| Tetracycline | 16 | 8 | 8 | 8 |
| Vancomycin | 0.25 | 0.25 | 0.25 | 4 |
| CFU/ml | 3.9*$10^5$ | 2.7*$10^5$ | 1.2*$10^5$ | |

*EFSA Journal 2012; 10(6): 2740

TABLE 5.3

MIC results for *B. subtilis* DSM 29870

| Antibiotic | MIC 1 µg/ml | MIC 2 µg/ml | MIC 3 µg/ml | EFSA* breakpoints µg/ml |
|---|---|---|---|---|
| Chloramphenicol | 4 | 8 | 4 | 8 |
| Clindamycin | 0.25 | 0.25 | 0.25 | 4 |
| Erythromycin | 0.125 | 0.125 | 0.125 | 4 |
| Gentamycin | 0.25 | 0.125 | 0.25 | 4 |
| Kanamycin | 2 | 1 | 2 | 8 |
| Streptomycin | 4 | 4 | 8 | 8 |
| Tetracycline | 0.25 | 0.25 | 0.25 | 8 |
| Vancomycin | 0.25 | 0.25 | 0.25 | 4 |
| CFU/ml | 4.2*$10^5$ | 2.1*$10^5$ | 1.4*$10^5$ | |

*EFSA Journal 2012; 10(6): 2740

TABLE 5.4

MIC results for *B. amyloliquefaciens* DSM 29872

| Antibiotic | MIC 2 µg/ml | MIC 3 µg/ml | MIC 4 µg/ml | MIC 5 µg/ml | EFSA* breakpoints µg/ml |
|---|---|---|---|---|---|
| Chloramphenicol | 4 | 4 | 4 | 4 | 8 |
| Clindamycin | 0.5 | 0.5 | 0.5 | 0.5 | 4 |
| Erythromycin | 0.06 | 0.125 | 0.06 | 0.06 | 4 |
| Gentamycin | 0.06 | 0.06 | 0.125 | 0.125 | 4 |
| Kanamycin | 1 | 0.5 | 2 | 1 | 8 |
| Streptomycin | 8 (32) | 8 | 32 | >64 | 8 |
| Tetracycline | 0.25 | 0.25 | 0.125 | 0.125 | 8 |
| Vancomycin | 0.25 | 0.25 | 0.125 | 0.125 | 4 |
| CFU/ml | $2.7*10^5$ | $1.5*10^5$ | $4.7*10^5$ | $6.3*10^5$ | |

*EFSA Journal 2012; 10(6): 2740

TABLE 5.5

MIC results for *S. aureus* ATCC 29213

| Antibiotic | MIC 1 µg/ml | MIC 2 µg/ml | MIC 3 µg/ml | MIC 4 µg/ml | MIC 5 µg/ml | CLSI* breakpoints µg/ml |
|---|---|---|---|---|---|---|
| Chloramphenicol | 8-16 | 16 | 8 | 16 | 16 | 2-16 |
| Clindamycin | 0.125 | 0.25 | 0.125 | 0.06 | 0.06 | 0.06-0.25 |
| Erythromycin | 0.5 | 0.5 | 0.5 | 0.5 | 0.5 | 0.25-1 |
| Gentamycin | 0.5 | 0.5 | 0.5 | 1 | 1 | 0.12-1 |
| Kanamycin | 4 | 4 | 4 | 4 | 4 | 1-4 |
| Streptomycin | 8 | 8 | 8 | 16 | 8 | No information |
| Tetracycline | 0.5 | 1 | 1 | 0.5 | 0.5 | 0.12-1 |
| Vancomycin | 0.5 | 1 | 1 | 1 | 1 | 0.5-2 |
| CFU/ml | $5.2*10^5$ | $7.0*10^5$ | $7.0*10^5$ | $7.3*10^5$ | $4.3*10^5$ | |

*M100-S24 Performance Standards for Antimicrobial Susceptibility Testing; informational Supplement, 2014

Example 6: Enzyme Activity

Preparation of Overnight Pre-Cultures

Overnight cultivation was made in a 96-deep well plate with 1.25 mL of LB broth (Difco; BD #244610) per well. Each strain was tested in duplicate and inoculated with a single colony from a pure Standard Methods Agar plate (SMA plates, Smith River Biologicals #11-00450). Before incubation, a single sterile Aeraseal breathable seal (Fisher #50-212-463) was placed on top of the plate, and the plate was incubated with shaking at 35° C. overnight under aerobic conditions.

Determination of Anaerobic Growth

SMA plates were streaked from the overnight cultures using a 10 µL inoculating loop. Up to four strains were streaked per plate, into separate quadrants.

Plates were incubated at 39° C. in an AnaeroJar (Thermo Scientific Oxoid, Fisher #OXAG0025A) along with an AnaeroGen sachet (Thermo Scientific Oxoid, Fisher #OXAN0025A) to maintain anaerobic conditions (~0.1% oxygen). Work was performed under aseptic conditions in biological hood, using sterile materials.

Enzyme Activity Determination Using AZCL-Substrate Agar Plates

Preparation of media with AZCL substrates which can be autoclaved AZCL-cellulose (AZCL-HE-Cellulose, 1-AZ-CEL, Megazyme), arabinoxylan (AZCL-Arabinoxylan, wheat, I-AZWAX, Megazyme), arabinan (AZCL-Arabinan, debranched, I-AZDAR, Megazyme):

Into two (2) 500 mL beakers, 300 mL of 0.1× and 1×LB agar were prepared for each beaker, with a magnetic stir bars added to each. While stirring, 100 mL of LB condition from the beakers were added to three (3) 250 mL Wheaton bottles, thus giving 3 bottles with 0.1× LB and 3 bottles with 1×LB. AZCL-cellulose, arabinan, and arabinoxylan were then added separately to each of a 1× and a 0.1× bottle with stirring. A total of 0.05 grams of substrate is added per 100 mL of media. If more than 100 mL of media is being used, the amount of substrate added is adjusted by using the 0.05 g/100 mL ratio. The media were autoclaved to sterilize. Note: Only these three AZCL substrates can be autoclaved without obvious dye release indicating substrate instability. After autoclaving, media is kept at ≥50° C. until ready to pour plates. The pH was checked, and if necessary adjusted to pH 7 using 10% HCl or 2N NaOH, maintaining sterility.

Preparation of Media with AZCL Substrates which Can't be Autoclaved

These substrates were: AZCL-amylose (I-AZAMY, Megazyme), AZCL-casein (I-AZCAS, Megazyme), AZCL-xylan (Xylan, birchwood (I-AZXBW, Megazyme)

Into two (2) 1000 mL Wheaton bottles, 400 mL of 0.1×LB and 1×LB was prepared and a magnetic stir bar was added to each. The media was autoclaved to sterilize, prior to adding AZCL reagent. After autoclaving, media was kept at 50-55° C. until ready to add AZCL substrate and pour plates. The pH was checked, and if necessary adjusted to pH 7 using 10% HCl or 2N NaOH, maintaining sterility.

Pouring AZCL Substrate Media Agar Plates

Work was performed under aseptic conditions in biological hood, using sterile materials. These steps were done relatively quickly, so that the agar did not solidify before transferring into the 96-well plate.

For substrates which could be autoclaved (AZCL-cellulose, AZCL-arabinoxylan, AZCL-arabinan): The warm (~50° C.), autoclaved liquid agar media was magnetically stirred in order to suspend the insoluble AZCL substrate. An aliquot was transferred to a sterile solution basin (Periodic mixing of the material in the solution basin was necessary to keep the substrate suspended.) A repeating, multi-channel pipette (e.g. Matrix 1250 µL pipet along with the corresponding 1250 µL sterile pipet tips) was used to dispense 180 µL into each well of a sterile 96-well plate. A set of tips would typically last for up to six columns per plate. Once the plate was filled, a sterile lid was added, and it was allowed to solidify. One plate was made for each substrate (AZCL-cellulose, AZCL-arabinoxylan, AZCL-arabinan) and condition (0.1× and 1×LB).

For the substrates that could not be autoclaved (AZCL-amylose, AZCL-casein, AZCL-xylan): Into a sterile 250 mL beaker with magnetic stir-bar was added 100 mL of warm, sterile 0.1× or 1×LB media (no AZCL substrate added). With stirring, add 0.05 mg of AZCL substrate, and continue stirring until re-suspended. It may help to add the substrate slowly at first. Once substrate was re-suspended, it was poured into solution basin and added to plates as described above. One plate was made for each substrate (AZCL-cellulose, AZCL-arabinoxylan, AZCL-arabinan) and condition (0.1× and 1×LB).

Inoculating the 96-Well Plates, Incubation, and Evaluation

Work was performed under aseptic conditions in biological hood, using sterile materials. The AZCL substrate agar plates were inoculated by applying 2 µL of overnight culture that was dispensed on top of the agar. The added liquid should be visible on top of the agar. When moving to the next plate, be sure that there are no drops left at the end of the pipet tips to ensure that each well has been inoculated. Repeat for all AZCL substrate plates. Control enzyme dilutions were prepared, each at $1/100$, diluting in sterile phosphate dilution buffer: 10 µL enzyme preparation+990 µL buffer. Control enzyme wells were then inoculated with 10 µL of the appropriate enzyme dilution for each substrate

TABLE 6.1

Enzymes and respective substrates

| Enzyme | Substrate |
|---|---|
| Amylase | Amylose |
| Arabinase | Arabinan |
| Cellulase | Cellulose |
| Protease | Casein |
| Xylanase | Arabinoxylan, Xylan |

TABLE 6.2

Enzyme production under aerobic conditions

| | 30° C. Aerobic, 24 h | | | | | |
|---|---|---|---|---|---|---|
| organism ID | Amylose | Arabinan | Arabinoxylan | Casein | Cellulose | Xylan |
| DSM 29869 | + | + | + | + | − | + |
| DSM 29870 | + | + | + | + | − | + |
| DSM 29871 | + | + | + | + | + | + |
| DSM 29872 | + | + | + | + | − | + |

TABLE 6.3

Enzyme production under anaerobic conditions, 24 hours

| | 30° C. Anaerobic, 24 h | | | | | |
|---|---|---|---|---|---|---|
| organism ID | Amylose | Arabinan | Arabinoxylan | Casein | Cellulose | Xylan |
| DSM 29869 | + | + | + | − | − | + |
| DSM 29870 | + | + | +/− | + | − | + |
| DSM 29871 | − | + | + | − | + | + |
| DSM 29872 | + | + | + | − | − | + |

TABLE 6.4

Enzyme production under anaerobic conditions, 48 hours

| | 30° C. Anaerobic, 48 h | | | | | |
|---|---|---|---|---|---|---|
| organism ID | Amylose | Arabinan | Arabinoxylan | Casein | Cellulose | Xylan |
| DSM 29869 | + | + | + | + | − | + |
| DSM 29870 | + | + | +/− | + | − | + |
| DSM 29871 | − | + | + | − | + | + |
| DSM 29872 | + | + | + | − | − | + |

Example 7: Efficacy of the DSM 29870 Strain in *Clostridium perfringens* Challenge Conditions Material and Methods Three independent battery studies have been conducted to evaluate the influence of the strain DSM 29870 on the development of an induced necrotic enteritis.

In each experiment, a total of 256 one day-old male broiler chickens Cobb×Cobb were allocated to Petersime battery cages (8 birds/cage). Cages were used in factorial and completely randomized design with 8 cages per treatment (i.e. 64 animals/treatment).

An unmedicated corn/soybean meal-based commercial broiler starter ration was formulated (Table 7.1). Feed and water were available ad libitum throughout the trials.

TABLE 7.1

Composition of the basal experimental diet[4] (starter d 1-d 28)

|  | Starter (0-28) |
|---|---|
| Ingredients |  |
| Corn, yellow, ground | 56.12 |
| Soybean meal (48) | 37.50 |
| Fat, poultry | 3.00 |
| Dicalcium phosphate | 1.75 |
| Limestone | 0.80 |
| Salt | 0.30 |
| Vitamin premix[1] | 0.25 |
| DL-Methionine | 0.20 |
| Trace mineral premix[2] | 0.08 |
| Calculated Nutritional Content |  |
| ME, kcal/kg | 3.096 |
| Protein, % | 22.30 |
| Lysine, % | 1.180 |
| Methionine, % | 0.530 |
| Met + Cys, %[3] | 0.890 |

[1]Vitamin mix provided the following (per kg of diet): thiamin•mononitrate, 2.4 mg; nicotinic acid, 44 mg; riboflavin, 4.4 mg; D-Ca pantothenate, 12 mg; vitamin $B_{12}$ (cobalamin), 12.0 µg; pyridoxine•HCL, 4.7 mg; D-biotin, 0.11 mg; folic acid, 5.5 mg; menadione sodium bisulfite complex, 3.34 mg; choline chloride, 220 mg; cholecalciferol, 27.5 ug; trans-retinyl acetate, 1,892 ug; all-rac α tocopheryl acetate, 11 mg; ethoxyquin, 125 mg.
[2]Trace mineral mix provided the following (per kg of diet): manganese ($MnSO_4$•$H_2O$), 60 mg; iron ($FeSO_4$•$7H_2O$), 30 mg; zinc (ZnO), 50 mg; copper ($CuSO_4$•$5H_2O$), 5 mg; iodine (ethylene diamine dihydroiodide), 0.15 mg; selenium ($NaSeO_3$), 0.3 mg.
[3]Met = methionine; Cys = cysteine.
[4]The basal feed will not contain any probiotic/prebiotic feed additives, NSPases, coccidiostats or antibiotic growth promoter.

The 4 experimental groups consisted in (Table 7.2): T1, non-infected and non-treated animals; T2, *C. perfringens* infected and non-treated animals; T3, *C. perfringens* infected animals fed with the basal diet containing bacitracin (included at 50 ppm, from d1 to d28); T4, *C. perfringens* infected animals fed with the basal diet containing the DSM 29870 strain (included at $1.10^9$ CFU/kg of feed in trial 1 and 5.108 CFU/kg of feed in trial 2 and 3, from d1 to d28).

TABLE 7.2

Experimental treatments

| Treatments | |
|---|---|
| T1 | Non-infected, non-treated |
| T2 | Infected, non-treated |
| T3 | Infected, bacitracin |
| T4 | Infected, DSM 29870 |

On day 14, all birds were orally inoculated with a coccidial inoculum containing approximately 5,000 oocysts of *Eimeria maxima* per bird.

Once daily on d19, d20 and d21, all birds, except T1, were administered (by oral gavage) 1 mL of a fresh broth culture of *C. perfringens*.

On d21, three birds from each cage were selected, sacrificed, weighed, and examined for the degree of presence of necrotic enteritis lesions. The scoring was based on a 0 to 3 score, with 0 being normal and 3 being the most severe.

The live body weight and the feed were recorded at the start (d1) and the end of the experiment (d28), on a cage basis, to calculate performance:

Body Weight Gain (BWG)=(Live Body Weight)$_{d28}$−(Live Body Weight)$_{d1}$

Feed Conversion Ratio (FCR)=ratio between feed consumed and weight gained

Mortality was recorded daily and the FCR was adjusted accordingly.

Necrotic enteritis lesion scores, total mortality and % of dead birds with necrotic enteritis lesions were also calculated Data (n=32) were subjected to an ANOVA, with complete randomized block design using the ANOVA procedure of XLSTAT (Addinsoft 1995-2014) to establish differences between diets. Pen was considered as the experimental unit. The model included diets (n=4) and block as fixed effect. Results are reported as least square means. LS means were assumed to be different at P s 0.05.

Experimental Results

The results obtained on performance, necrotic enteritis lesion scores, mortality and % of dead birds with necrotic enteritis lesions parameters are shown in Tables 7.3.

TABLES 7.3

Effect of dietary supplementation of the strain DSM 29870 on the negative impact on production parameters due to induced necrotic enteritis in three independent trials.

| Trial 1 | BWG[5] (g/bird) (d 1-d 28) | FCR[5] (d 1-d 28) | Lesion score[6] (d 21) | Total mortality (%) (d 1-d 28) | Dead birds with necrotic enteritis lesions (%) (d 1-d 28) |
|---|---|---|---|---|---|
| T1[1] | 720a | 1.666c | 0.0a | 7.5b | 0.0b |
| T2[2] | 549b | 2.071a | 0.2a | 27.5a | 17.2a |
| T3[3] | 633ab | 1.813bc | 0.2a | 5.0b | 1.6b |
| T4[4] | 628ab | 1.843bc | 0.3a | 5.0b | 3.1b |

[1]Non-infected, non-treated group fed with the basal diet.
[2]Infected, non-treated group fed with the basal diet.
[3]Infected group fed with the basal diet supplemented with bacitracin (50 ppm).
[4]Infected group fed with the basal diet supplemented with DSM 29870 ($1.10^9$ CFU/kg of feed).
[5]Means from 8 replicates of 8 birds per cage for each group. Raw data (n = 32) were analyzed using variance analysis with block (n = 8) and treatments (n = 4) as fixed effect.
[6]Means from 8 replicates of 3 birds per cage for each group. Raw data (n = 32) were analyzed using variance analysis with block (n = 8) and treatments (n = 4) as fixed effect.
a,b,cValues with different superscripts are significantly (P < 0.05) different from each other.

TABLES 7.3-continued

Effect of dietary supplementation of the strain DSM 29870 on the negative impact on production parameters due to induced necrotic enteritis in three independent trials.

| Trial 2 | BWG[5] (g/bird) (d 1-d 28) | FCR[5] (d 1-d 28) | Lesion score[6] (d 21) | Total mortality (%) (d 1-d 28) | Dead birds with necrotic enteritis lesions (%) (d 1-d 28) |
|---|---|---|---|---|---|
| T1 | 685a | 1.692b | 0.0d | 2.5c | 0.0c |
| T2 | 435c | 2.404a | 1.2a | 32.5a | 20.3a |
| T3 | 665ab | 1.759b | 0.6b | 12.5bc | 6.3c |
| T4 | 654ab | 1.768b | 0.4bc | 25.0ab | 9.4bc |

[1] Non-infected, non-treated group fed with the basal diet.
[2] Infected, non-treated group fed with the basal diet.
[3] Infected group fed with the basal diet supplemented with bacitracin (50 ppm).
[4] Infected group fed with the basal diet supplemented with DSM 29870 ($5.10^8$ CFU/kg of feed).
[5] Means from 8 replicates of 8 birds per cage for each group. Raw data (n = 32) were analyzed using variance analysis with block (n = 8) and treatments (n = 4) as fixed effect.
[6] Means from 8 replicates of 3 birds per cage for each group. Raw data (n = 32) were analyzed using variance analysis with block (n = 8) and treatments (n = 4) as fixed effect.
a,b,c Values with different superscripts are significantly ($P < 0.05$) different from each other.

| Trial 3 | BWG[5] (g/bird) (d 1-d 28) | FCR[5] (d 1-d 28) | Lesion score[6] (d 21) | Total mortality (%) (d 1-d 28) | Dead birds with necrotic enteritis lesions (%) (d 1-d 28) |
|---|---|---|---|---|---|
| T1 | 667a | 1.752c | 0.0b | 10.0a | 0.0c |
| T2 | 521b | 1.988a | 0.5a | 25.0a | 15.6a |
| T3 | 645a | 1.786bc | 0.6a | 15.0a | 4.7bc |
| T4 | 638a | 1.851b | 0.4a | 10.0a | 4.7bc |

[1] Non-infected, non-treated group fed with the basal diet.
[2] Infected, non-treated group fed with the basal diet.
[3] Infected group fed with the basal diet supplemented with bacitracin (50 ppm).
[4] Infected group fed with the basal diet supplemented with DSM 29870 ($5.10^8$ CFU/kg of feed).
[5] Means from 8 replicates of 8 birds per cage for each group. Raw data (n = 32) were analyzed using variance analysis with block (n = 8) and treatments (n = 4) as fixed effect.
[6] Means from 8 replicates of 3 birds per cage for each group. Raw data (n = 32) were analyzed using variance analysis with block (n = 8) and treatments (n = 4) as fixed effect.
a,b,c Values with different superscripts are significantly ($P < 0.05$) different from each other.

The data obtained from the three challenge studies showed that the strain DSM 29870 can counteract the negative impact of an induced necrotic enteritis on the production parameters with a significant effect in all challenge trials on the FCR and the mortality due to necrotic enteritis, relative to the positive control group (non-infected, non-treated animals).

Furthermore, there was no significant difference between the DSM 29870 fed group and the bacitracin fed group with regards to all parameters measured in these trials.

The challenge studies described above showed that the administration of the DSM 29870 strain could prevent necrotic enteritis in broiler chickens.

Example 8: First Performance Trial with Broiler Chickens (521)

Material and Methods

A total of 2000 one day-old male broiler chickens Cobb 500 were individually weighed (body weight 42 g±1 g) and allocated in floor pens (50 birds/pen). Pens were used in factorial and completely randomized design with 8 pens per treatment (i.e. 400 animals/treatment). The experimental treatments consisted in (Table 8.1): T1, negative control basal diets; T2, basal diets containing the strain DSM 29870 (included at 5.108 CFU/kg of feed, from d1 to d35); T3, basal diets containing the strain DSM 29871 (included at $5.10^8$ CFU/kg of feed, from d1 to d35); T4 basal diets containing the strain DSM 29872 (included at $5.10^8$ CFU/kg of feed, from d1 to d35); T5, basal diet containing a marketed probiotic, GalliPro Max (included at the commercial dose, $8.10^8$ CFU/kg of feed, from d1 to d35).

Basal diets consisted in 3 phases feeding program: starter phase (from 1 to day 12), grower phase (from 13 to day 28) and finisher phase (from 29 to day 35). Every phase was formulated to meet or exceed animal requirement and agree with standard commercial US corn-soybean meal-based broiler diets. The dietary and raw material composition of these diets is given in Table 8.2. All experimental diets include phytase (Ronozyme P, 250 FYT/kg) and did not contain any coccidiostat, NSPase or growth promoting substance. Feed and water were available ad libitum throughout the trial.

TABLE 8.1

| Experimental treatments | |
|---|---|
| Treatments | |
| T1 | Control |
| T2 | T1 + DSM 29870 |
| T3 | T1 + DSM 29871 |
| T4 | T1 + DSM 29872 |
| T5 | T1 + GalliPro Max |

TABLE 8.2

Composition of the basal experimental diets

| | Starter (0-12 d) | Grower (13-28 d) % | Finisher (29-35 d) |
|---|---|---|---|
| Ingredients | | | |
| Corn, yellow, grain | 64.673 | 66.460 | 68.491 |
| Soybean meal, dehulled, solvent | 29.020 | 26.662 | 24.677 |
| Ampro 55 (animal by-product 55% protein) | 2.500 | 3.000 | 3.000 |
| Calcium carbonate | 0.886 | 0.735 | 0.684 |
| Fat, vegetable | 0.883 | 1.485 | 1.702 |
| Dicalcium phosphate | 0.706 | 0.612 | 0.500 |
| Salt, plain (NaCl) | 0.439 | 0.435 | 0.436 |
| Methionine MHA | 0.358 | 0.259 | 0.221 |
| L-Lysine | 0.273 | 0.208 | 0.145 |
| L-Threonine 98.5 | 0.103 | 0.000 | 0.000 |
| Trace Mineral[1] | 0.075 | 0.075 | 0.075 |
| Vitamin premix [2] | 0.065 | 0.050 | 0.050 |
| Ronozyme P-(ct) | 0.019 | 0.019 | 0.019 |
| Calculated Nutritional Content | | | |
| ME (kcal/kg) | 3,067 | 3,130 | 3,165 |
| Crude protein (%) | 20.96 | 20.03 | 19.16 |
| Dig. Lysine (%) | 1.20 | 1.10 | 1.00 |
| Dig. Methionine (%) | 0.61 | 0.52 | 0.48 |
| Dig. TSAA (%) | 0.90 | 0.80 | 0.75 |
| Dig. Threonine (%) | 0.81 | 0.68 | 0.65 |
| Calcium (%) | 0.90 | 0.85 | 0.8 |
| Avail. phosphorus (%) | 0.42 | 0.42 | 0.4 |

[1]Vitamin mix will provide the following (per kg of diet): thiamin•mononitrate, 2.4 mg; nicotinic acid, 44 mg; riboflavin, 4.4 mg; D-Ca pantothenate, 12 mg; vitamin $B_{12}$ (cobalamin), 12.0 μg; pyridoxine•HCL, 4.7 mg; D-biotin, 0.11 mg; folic acid, 5.5 mg; menadione sodium bisulfite complex, 3.34 mg; choline chloride, 220 mg; cholecalciferol, 27.5 ug; trans-retinyl acetate, 1,892 ug; all-rac α tocopheryl acetate, 11 mg; ethoxyquin, 125 mg.
[2] Trace mineral mix provided the following (per kg of diet): manganese ($MnSO_4 \cdot H_2O$), 60 mg; iron ($FeSO_4 \cdot 7H_2O$), 30 mg; zinc (ZnO), 50 mg; copper ($CuSO_4 \cdot 5H_2O$), 5 mg; iodine (ethylene diamine dihydroiodide), 0.15 mg; selenium ($NaSeO_3$), 0.3 mg.

Data (n=40) were subjected to an ANOVA, with complete randomized block design using the ANOVA procedure of XLSTAT (Addinsoft 1995-2014) to establish differences between diets. Pen was considered as the experimental unit. The model included diets (n=5) and block as fixed effect. Results are reported as least square means. LS means were assumed to be different at P s 0.05.

Similar calculations were realized in the example 9 and 10.

Experimental Results

The results obtained on performance parameters for the whole experimental period are shown in Table 8.3.

Feed additives did not significantly affect animal feed intake relative to the control. Body weight was slightly increased using the NZB strains whereas GalliPro Max tended to decrease this parameter.

The DSM 29870, DSM 29871 and DSM 29872 strains also improved significantly the feed conversion ratio by 1.6%, 1.5% and 1.9%, respectively, with no significant differences between the groups fed with NZB strains. GalliPro Max had only a slight and non-significant effect on the feed conversion ratio.

None of the probiotic tested here had a significant effect on the mortality level.

Example 9: Second Performance Trial with Broiler Chickens (522)

Material and Methods

A total of 900 one day-old male broiler chickens Ross 708 were individually weighed (body weight 47.1 g±1.1 g) and allocated in floor pens (15 birds/pens). Pens were used in factorial and completely randomized design with 12 pens per treatment (i.e. 180 animals/treatment). The 5 experimental treatments consisted in (Table 9.1): T1, negative control basal diets; T2, basal diets containing the strain DSM 29870 (included at $5.10^8$ CFU/kg of feed, from d1 to d35); T3, basal diets containing the strain DSM 29871 (included at $5.10^8$ CFU/kg of feed, from d1 to d35); T4 basal diets containing the strain DSM 29872 (included at $5.10^8$ CFU/kg of feed, from d1 to d35); T5, basal diet containing a marketed probiotic, GalliPro Max (included at the commercial dose, $8.10^8$ CFU/kg of feed, from d1 to d35).

Basal diets consisted in 3 phases feeding program: starter phase (from 1 to day 14), grower phase (from 15 to day 21) and finisher phase (from 22 to day 35). Every phases were formulated to meet or exceed animal requirement and agree with standard commercial US corn-soybean meal-based broiler diets. The dietary and raw material composition of

TABLE 8.3

Effect of dietary supplementation of the strains DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3245a | 3256a | 3221a | 3263a | 3203a |
| Relative to the control | — | +0.3% | −0.7% | +0.6% | −1.3% |
| BWG (g/bird) | 1987ab | 2026ab | 2002ab | 2038a | 1973b |
| Relative to the control | — | +2.0% | +0.8% | +2.6% | −0.7% |
| FCR | 1.633a | 1.607b | 1.609b | 1.602b | 1.624ab |
| Relative to the control | — | −1.6% | −1.5% | −2.0% | −0.6% |
| Mortality (%) | 3.25a | 3.50a | 5.25a | 4.5a | 6.25a |

[1]Group fed with the basal diet.
[2]DSM 29870/29871/29872 supplemented group fed with the basal diet including strain DSM 29870/29871/29872 at $5.10^8$ CFU/kg of feed.
[3]GalliPro Max supplemented group fed with the basal diet including GalliPro Max at $8.10^8$ CFU/kg of feed.
[4]Means from 8 replicates of 50 birds per pen for each group. Raw data (n = 24) were analyzed using variance analysis with block (n = 8) and treatments (n = 3) as fixed effect.
a, b, c Values with different superscripts are significantly (P < 0.05) different from each other.

these diets is given in Table 9.2. All experimental diets included vitamin and mineral premixes, but did not contain any coccidiostat, NSPase, phytase or growth promoting substance. Feed and water were available ad libitum throughout the trial.

TABLE 9.1

Experimental treatments

| Treatments | |
|---|---|
| T1 | Control |
| T2 | T1 + DSM 29870 |
| T3 | T1 + DSM 29871 |
| T4 | T1 + DSM 29872 |
| T5 | T1 + GalliPro Max |

TABLE 9.2

Composition of the basal experimental diets

| | Starter (0-14 d) | Grower (15-21 d) % | Finisher (22-35 d) |
|---|---|---|---|
| Ingredients | | | |
| Corn | 57.59 | 59.20 | 62.30 |
| Wheat Flour | 1.00 | 1.00 | 1.00 |

TABLE 9.2-continued

Composition of the basal experimental diets

| | Starter (0-14 d) | Grower (15-21 d) % | Finisher (22-35 d) |
|---|---|---|---|
| Soybean Meal (46% CP) | 30.00 | 28.00 | 24.50 |
| Poultry Meal | 5.00 | 5.00 | 5.00 |
| Poultry Fat | 2.10 | 2.86 | 3.52 |
| Limestone (36% Ca) | 1.05 | 1.02 | 0.98 |
| Dicalcium Phosphate (18% P) | 1.76 | 1.52 | 1.42 |
| Salt | 0.35 | 0.32 | 0.29 |
| Sodium Bicarbonate | 0.16 | 0.14 | 0.11 |
| L-Lysine HCL (78%) | 0.23 | 0.22 | 0.21 |
| DL-Methionine (99%) | 0.36 | 0.33 | 0.29 |
| L-Threonine (98%) | 0.05 | 0.04 | 0.03 |
| Selenium premix | 0.05 | 0.05 | 0.05 |
| Vitamin Mix | 0.15 | 0.15 | 0.15 |
| Mineral Mix | 0.15 | 0.15 | 0.15 |
| Calculated Nutritional Content | | | |
| ME (kcal/kg) | 2968 | 3032 | 3096 |
| Crude Protein (%) | 23.3 | 22.4 | 20.78 |
| Lysine (%) | 1.35 | 1.29 | 1.18 |
| Methionine (%) | 0.69 | 0.65 | 0.59 |
| Met + Cys (%) | 1.05 | 1.00 | 0.92 |
| Threonine (%) | 0.86 | 0.81 | 0.75 |
| Calcium (%) | 1.03 | 0.96 | 0.91 |
| Phosphorus Avail. (%) | 0.46 | 0.41 | 0.39 |

[1]Vitamin mix will provide the following (per kg of diet): vitamin A, 13 227 513 IU; vitamin D3, 3 968 254 IU; vitamin E, 66 138 IU; vitamin $B_{12}$, 40 mg; biotin, 254 mg; menadione, 3 968 mg; thiamine, 3 968 mg; riboflavin, 13 228 mg; d-Pantothenic Acid, 22 046 mg; pyridoxine, 7 937 mg; niacin, 110 229 mg; folic acid, 2 205 mg; Selenium Premix: selenium, 600 ppm + calcium, 36%
[2]Trace mineral mix provided the following (per kg of diet): calcium, Min: 15.7% and Max: 18.7%; manganese (Mn), 6.0%; zinc (Zn), 6.0%; iron (Fe), 4.0%; copper (Cu), 5000 ppm; iodine (I), 1250 ppm; cobalt (Co), 500 ppm Experimental Results The results obtained on performance parameters for the whole experimental period are shown in Table 9.3.

TABLE 9.3

Effect of dietary supplementation of the strains DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3573a | 3542a | 3606a | 3515a | 3541a |
| Relative to the control | — | −0.9% | +0.9% | −1.0% | −0.9% |
| BWG (g/bird) | 2361a | 2416b | 2401ab | 2424b | 2398ab |
| Relative to the control | — | +2.3% | +1.7% | +2.6% | +1.5% |
| FCR | 1.513a | 1.467b | 1.501bc | 1.451a | 1.477ab |
| Relative to the control | — | −3.6% | −0.8% | −4.2% | −2.4% |
| Mortality (%) | 15.6ab | 7.8a | 11.7ab | 19.4b | 10.0a |

[1]Group fed with the basal diet
[2]DSM 29870/29871/29872 supplemented group fed with the basal diet including strain DSM 29870/29871/29872 at $5.10^8$ CFU/kg of feed.
[3]GalliPro Max supplemented group fed with the basal diet including GalliPro Max at $8.10^8$ CFU/kg of feed.
[4]Means from 12 replicates of 15 birds per pen for each group. Raw data (n = 36) were analyzed using variance analysis with block (n = 12) and treatments (n = 3) as fixed effect.
a,b,cValues with different superscripts are significantly (P < 0.05) different from each other Also in this experiment, the administration of the strains DSM 29870, DSM 29871, DSM 29872 and GalliPro Max did not significantly reduce the feed intake, but improved the body weight gain by 2.3%, 1.7%, 2.6% and 1.5%, respectively. Therefore, difference relatively to control was significant for DSM 29870 and DSM 29872.

The strains DSM 29870 and DSM 29872 improved significantly the feed conversion ratio by 3.6% and 4.2%, respectively. DSM 29871 and GalliPro Max also improved (slightly for DSM 29871) the feed conversion ratio in this experiment, but not significantly.

The strain DSM 29870 allowed a decrease of the mortality level in a numerically higher manner than GalliPro Max.

Example 10: Third Performance Trial with Broiler Chickens (051)

Material and Methods

A total of 1080 one day-old male broiler chickens Ross PM3 were individually weighed (body weight 42±3.5 g) and allocated in floor pens (18 birds/pens). Pens were used in factorial and completely randomized design with 12 pens per treatment (i.e. 216 animals/treatment). The 3 experimental treatments consisted in (Table 10.1): T1, negative control basal diets; T2, basal diets containing the strain DSM 29870 (included at $5.10^8$ CFU/kg of feed, from d1 to d35); T3, basal diets containing the strain DSM 29871 (included at $5.10^8$ CFU/kg of feed, from d1 to d35); T4 basal diets containing the strain DSM 29872 (included at $5.10^8$ CFU/kg of feed, from d1 to d35); T5, basal diet containing a marketed probiotic, GalliPro Max (included at the commercial dose, $8.10^8$ CFU/kg of feed, from d1 to d35).

Basal diets consisted in 3 phases feeding program: starter phase (from 1 to day 21) and grower phase (from 22 to day 35). Every phase was formulated to meet or exceed animal requirement and agree with standard commercial EU corn-soybean meal-based broiler diets. The dietary and raw material composition of these diets is given in Table 10.2. All experimental diets included vitamin and mineral premixes, but did not contain any coccidiostat, NSPase, phytase or growth promoting substance. Feed and water were available ad libitum throughout the trial.

TABLE 10.1

Experimental treatments

| Treatments | |
|---|---|
| T1 | Control |
| T2 | T1 + DSM 29870 |
| T3 | T1 + DSM 29871 |
| T4 | T1 + DSM 29872 |
| T5 | T1 + GalliPro Max |

TABLE 10.2

Composition of the basal experimental diets

| | Starter (0-21 d) | Grower (22-35 d) |
|---|---|---|
| | % | |
| Ingredients | | |
| Maize | 51.68 | 55.58 |
| Soybean Meal (48% CP) | 39.03 | 34.55 |
| Soybean oil | 4.27 | 5.18 |
| DL-Methionine | 0.22 | 0.17 |
| Calcium carbonate | 1.05 | 1.05 |
| Dicalcium Phosphate | 1.78 | 1.5 |
| Salt | 0.37 | 0.37 |
| Wheat middlings | 1.00 | 1.00 |
| Premix[1] | 0.6 | 0.6 |
| Calculated Nutritional Content | | |
| ME (kcal/kg) | 3000 | 3100 |
| Crude Protein (%) | 22.25 | 20.5 |
| Fat (%) | 6.76 | 7.7 |
| Cellulose (%) | 3.15 | 3 |
| Minerals (%) | 5.74 | 5.3 |
| Lysine (%) | 1.25 | 1.13 |
| Methionine (%) | 0.55 | 0.48 |
| Met + Cys (%) | 0.92 | 0.83 |
| Threonine (%) | 0.87 | 0.8 |
| Calcium (%) | 0.93 | 0.85 |
| Total phosphorus | 0.7 | 0.63 |
| Phosphorus Avail. (%) | 0.38 | 0.33 |

[1]The premix will provide the following (per kg of diet): vitamin A, 12 000 IU; vitamin D3, 3 000 IU;, vitamin E = 300 IU;, vitamin K3, 3 mg; vitamin B, 2 mg; vitamin B2, 8 mg; vitamin B6, 3 mg; vitamin B12, 0.02 mg; folic acid, 1 mg; biotin, 0.2 mg; calcium pantothenate, 15 mg; nicotinic acid, 40 mg; manganese (Mn), 80 mg; zinc (Zn), 60 mg; iodine (I), 1 mg, iron (Fe), 80 mg; copper (Cu), 15 mg; cobalt (Co), 0.4 mg; selenium (Se), 0.2 mg; magnesium (Mg), 5 mg; Etoxyquin, 0.5 mg; BHA, 0.5 mg, citric acid, 5 mg; phosphoric acid, 5 mg.

Experimental Results

The results obtained on performance parameters for the whole experimental period are shown in Table 10.3.

TABLE 10.3

Effect of dietary supplementation of the strains DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3217a | 3295a | 3281a | 3230a | 3246a |
| Relative to the control | — | +2.4% | +2.0% | +0.4% | +0.9% |
| BWG (g/bird) | 2019b | 2149a | 2167a | 2124a | 2103ab |
| Relative to the control | — | +6.5% | +7.3% | +5.2% | +4.2% |
| FCR | 1.598a | 1.534b | 1.513b | 1.521b | 1.544b |
| Relative to the control | — | −4.0% | −5.3% | −4.8% | −3.4% |
| Mortality (%) | 11.1a | 9.7a | 8.3a | 6.5a | 7.4a |

[1]Group fed with the basal diet.
[2]DSM 29870/29871/29872 supplemented group fed with the basal diet including strain DSM 29870/29871/29872 at $5.10^8$ CFU/kg of feed.
[3]GalliPro Max supplemented group fed with the basal diet including GalliPro Max at $8.10^8$ CFU/kg of feed.
[4]Means from 12 replicates of 18 birds per pen for each group. Raw data (n = 36) were analyzed using variance analysis with block (n = 12) and treatments (n = 3) as fixed effect.
a,b,cValues with different superscripts are significantly (P < 0.05) different from each other.

In this experiment, the administration of the strains DSM 29870, DSM 29871, DSM 29872 (as GalliPro Max) had not significant effect on the feed intake, but led to the significant improvement of the body weight gain by 6.5%, 7.3% and 5.2%, respectively. GalliPro Max improved also the body weight gain (+4.2%), but not significantly.

All NZB strains improved significantly the feed conversion ratio by 4.0%, 5.3% and 4.8% (DSM 29870, DSM 29871 and DSM 29872, respectively) as GalliPro Max which reached 3.4% of improvement.

Regarding the mortality level, there were no significant differences between the treatments.

Example 11: Synthesis and Meta-Analysis

The results of the three performance experiments described above are summarized in Table 11.1.

TABLE 11.1

Results of the individual studies

| Trial | Treatments | FI (g/bird) | Relative to the control | BWG (g/bird) | Relative to the control | FCR | Relative to the control |
|---|---|---|---|---|---|---|---|
| 1 | Control | 3245a | — | 1987ab | — | 1.633a | — |
|   | DSM 29870 | 3256a | +0.3% | 2026ab | +2.0% | 1.607b | −1.6% |
|   | DSM 29871 | 3221a | −0.7% | 2002ab | +0.8% | 1.609b | −1.5% |
|   | DSM 29872 | 3263a | +0.6% | 2038a | +2.6% | 1.602b | −2.0% |
|   | GalliPro Max | 3203a | −1.3% | 1973b | −0.7% | 1.624ab | −0.6% |
| 2 | Control | 3573a | — | 2361a | — | 1.513a | — |
|   | DSM 29870 | 3542a | −0.9% | 2416b | +2.3% | 1.467b | −3.6% |
|   | DSM 29871 | 3606a | +0.9% | 2401ab | +1.7% | 1.501bc | −0.8% |
|   | DSM 29872 | 3515a | −1.0% | 2424b | +2.6% | 1.451a | −4.2% |
|   | GalliPro Max | 3541a | −0.9% | 2398ab | +1.5% | 1.477ab | −2.4% |
| 3 | Control | 3217a | — | 2019b | — | 1.598a | — |
|   | DSM 29870 | 3295a | +2.4% | 2149a | +6.5% | 1.534b | −4.0% |
|   | DSM 29871 | 3281a | +2.0% | 2167a | +7.3% | 1.513b | −5.3% |
|   | DSM 29872 | 3230a | +0.4% | 2124a | +5.2% | 1.521b | −4.8% |
|   | GalliPro Max | 3246a | +0.9% | 2103ab | +4.2% | 1.544b | −3.4% | a,b,c Values with different superscripts are significantly ($P < 0.05$) different from each other.

These trials having a similar experimental design, all the data obtained were pooled and combined in a meta-analysis (after having been tested for homogeneity). This meta-analysis involved 3 980 broilers in 160 replicates (32 replicates and 796 animals for each experimental group). The results are shown in Table 11.

Data (n=160) were subjected to a mixed model ANOVA, using the GLIMMIX procedure of SAS (SAS Institute, 2002-2012) to establish differences between diets. Pen was considered as the experimental unit. The model included diets (n=5) as fixed effect and experiment (n=3) as random effect. Results are reported as least square means. LS means were assumed to be different at P: 0.05.

TABLE 11.2 meta-analysis of three experiments showing the effect of dietary supplementation of the strain DSM 29870, DSM 29871 and DSM 29872 on broiler performance

| Parameters[4] | Control[1] | DSM 29870[2] supplemented group | DSM 29871[2] supplemented group | DSM 29872[2] supplemented group | GalliPro Max[3] supplemented group |
|---|---|---|---|---|---|
| FI (g/bird) | 3343a | 3360a | 3361a | 3356a | 3347a |
| Relative to the control | — | +0.5% | +0.5% | +0.4% | +0.1% |
| BWG (g/bird) | 2145b | 2208a | 2202ab | 2211a | 2171ab |
| Relative to the control | — | +2.9% | +2.6% | +3.0% | +1.2% |
| FCR | 1.560a | 1.530b | 1.53bc | 1.52c | 1.550ab |
| Relative to the control | — | −2.4% | −2.2% | −2.7% | −1.1% |

[1] Group fed with the basal diet
[2] DSM 29870/29871/29872 supplemented group fed with the basal diet including strain DSM 29870/29871/29872 at $5.10^8$ CFU/kg of feed.
[3] GalliPro Max supplemented group fed with the basal diet including GalliPro Max at $8.10^8$ CFU/kg of feed.
[4] Means from 32 observations for each experimental group (796 animals/group).
a,b,c Values with different superscripts are significantly ($P < 0.05$) different from each other.

This meta-analysis showed that the use of the strain DSM 29870, DSM 29871 or DSM 29872 in a corn/soybean meal-based diet significantly improved in average the body weight gain (+2.9%, +2.6% and +3.0%, respectively) and the feed conversion ratio (−2.4%, −2.2% and −2.7%, respectively) with no effect on the feed intake.

Conclusion

In the working examples above, positive effects of strain DSM 29870 have been demonstrated on broiler performances (i.e. body weight gain and feed conversion ratio) fed a corn/soybean meal-based diet.

All the data obtained from the experiments described in the above examples also showed that the effect of strain DSM 29870 on the feed conversion ratio is due to its effect on the body weight. These effects might be associated with either health effect or metabolism improvement.

GalliPro Max showed no significant effect on the body weight gain in any of the working examples above and showed significant and positive effect on feed conversion ratio in one third of the experiments.

In the experiments described in the above examples, the better effect of strain DSM 29870 compared to GalliPro Max on broilers performance has been demonstrated. The effect observed using DSM 29870 were in average twice those observed for GalliPro Max.

Example 12: Determination of Monensin Compatibility

Monensin compatibility of *Bacillus* strains DSM 29869, DSM 29870, DSM 29871, and DSM 29872 was determined using a modified broth micro dilution similar to the method described in the Example 5. Briefly, a single colony of *Bacillus* spp. (from overnight tryptic soy agar plates) was inoculated into Mueller Hinton Broth (MHB) and cultured overnight. Sterile media was the inoculated with the overnight culture and allowed to grow for 4 hours to test bacteria in log growth phase. Cultures were then diluted once more 1:200 into fresh MHB and 90 µL of this inoculated broth was added to the diluted monensin at the indicated concentrations. Prior art strains were also tested for comparison: NN019785, NN062266 (NRRL B-50013), NN062267 (NRRL B-50104), NN062278 (PTA-6507), NN062319 (FERM BP-1096), NN062440, NN062441 (DSM 17236), NN062439.

Strains:
*Bacillus amyloliquefaciens* DSM 29869
*Bacillus subtilis* DSM 29870
*Bacillus subtilis* DSM 29871
*Bacillus amyloliquefaciens* DSM 29872
*Bacillus licheniformis* NN019785
*Bacillus amyloliquefaciens* NN062266 (NRRL B-50013)
*Bacillus subtilis* NN062267 (NRRL B-50104)
*Bacillus subtilis* NN062278 (PTA-6507)
*Bacillus amyloliquefaciens* NN062319 (FERM BP-1096)
*Bacillus subtilis* NN062440
*Bacillus licheniformis* NN062441 (DSM 17236)
*Bacillus amyloliquefaciens* NN062439

Materials:
Monensin sodium salt (Sigma, CAS no. 22373-78-0, solubilized in 96% ethanol)
Mueller Hinton Broth (Becton, Dickinson and Company, 275730)
Tryptic soy agar (Becton, Dickinson and Company, 236920)
Micro titer plates: Costar plate, polypropylene, flat bottom, Corning, 3628
Borosilicate glass tubes: Kimbale, 16×125 mm, 73500-16125
Adhesive gas permeable seals: Thermo Scientific, AB-0718

Preparation of Bacteria:

*Bacillus* spp. were grown overnight on tryptic soy agar plates (40 g/L) at 37° C. Mueller Hinton broth (21 g/L) was dissolved in water and autoclaved in glass tubes containing 5 mL of broth each. A single colony of *Bacillus* spp. (from overnight plates) was inoculated into Mueller Hinton Broth (MHB) and incubated overnight at 37° C. shaking at 200 rpm. A 5 mL glass tube of fresh, sterile media was then inoculated with 25 mL of overnight culture and allowed to grow for 4 hours at 37° C. Cultures were then diluted once more 1:200 into fresh MHB. 90 µL of this inoculated broth was then added to the diluted antibiotic at the indicated concentrations.

Preparation of Assay Plates:

Monensin was diluted into 96% ethanol to a concentration of 800 µg/mL. This solution was then diluted 10-fold into sterile phosphate buffer to a concentration of 80 µg/mL. A two fold dilution series was prepared in MHB down to the concentration 2.5 µg/mL. 10 µl of each dilution and of each antibiotic was pipetted into a micro titer plate. Later, when the antibiotics were mixed with the suspension of bacteria, the samples were diluted 10× (10 µL sample in a total volume of 100 µl). This resulted in the final test range of 0.25-8 µg/ml.

90 µl of the bacterial suspensions were added to the assay plates. The assay plates were then covered with an adhesive glass permeable seal and incubated overnight at 37° C. shaking at 200 rpm. The maximum compatible concentration was determined similar to a MIC analysis as the concentration above that which inhibited 80% of bacteria as detected by the unaided eye.

Results:

A potential challenge of delivering *Bacillus* spp. in feed is the common use of antibiotics as growth promoters in feed. Therefore it is necessary to determine the compatibility of strains with commonly-used feed antibiotics in order to identify any potential conflicts with use as a direct fed microbial. Therefore, the monensin compatibility of *Bacillus* strains DSM 29869, DSM 29870, DSM 29871, and DSM 29872 were determined along with prior art strains. *Bacillus* strains DSM 29869, DSM 29870, DSM 29871, and DSM 29872 indicated a higher level of compatibility with monensin than most of the prior art strains included herein: NN019785, NN062266 (NRRL B-50013), NN062267 (NRRL B-50104), NN062278 (PTA-6507), NN062319 (FERM BP-1096), NN062440, NN062441 (DSM 17236), NN062439.

TABLE 12.1

Monensin compatibility results

| | | Species | Product Name | Monensin (µg/mL) |
|---|---|---|---|---|
| NN062677 | DSM29870 | *Bacillus subtilis* | | 2.7 |
| NN062673 | DSM29871 | *Bacillus subtilis* | | 2.0 |

TABLE 12.1-continued

Monensin compatibility results

|  |  | Species | Product Name | Monensin (μg/mL) |
|---|---|---|---|---|
| NN062683 | DSM29872 | *Bacillus amyloliquefaciens* |  | 4.0 |
| NN062676 | DSM29869 | *Bacillus amyloliquefaciens* |  | 2.0 |
| NN019785 |  | *Bacillus licheniformis* | BioPlus 2B (Chr. Hansen) | 0.8 |
| NN062266 | NRRL B-50013 | *Bacillus amyloliquefaciens* | Eviva Pro (Dupont) | 1.1 |
| NN062267 | NRRL B-50104 | *Bacillus subtilis* | Eviva Pro (Dupont) | 1.1 |
| NN062278 | PTA-6507 | *Bacillus subtilis* | Eviva Pro (Dupont) | 1.4 |
| NN062319 | FERM BP-1096 | *Bacillus amyloliquefaciens* | Calsporin (Calpis) | 2.2 |
| NN062440 |  | *Bacillus subtilis* | GalliPro Max (Chr. Hansen) | 0.4 |
| NN062441 | DSM 17236 | *Bacillus licheniformis* | GalliPro Tect (Chr. Hansen) | 0.9 |
| NN062439 |  | *Bacillus amyloliquefaciens* | Clostat (Kemin) | 2.1 |

What is claimed is:

1. An animal feed or an animal feed additive comprising forage and at least one *Bacillus* strain selected from the group consisting of
   a *Bacillus* strain having deposit accession number DSM 29870;
   a *Bacillus* strain having deposit accession number DSM 29869;
   a *Bacillus* strain having deposit accession number DSM 29871; and
   a *Bacillus* strain having deposit accession number DSM 29872,
wherein at least one *Bacillus* strain is present in the animal feed or animal feed additive in an amount sufficient to have antimicrobial activity against *Clostridium perfringens* and to improve body weight gain and/or feed conversion rate in chickens fed with the animal feed or animal feed additive.

2. The animal feed or the animal feed additive according to claim 1, wherein the at least one *Bacillus* strain comprises the *Bacillus* strain having deposit accession number DSM 29870.

3. The animal feed or the animal feed additive according to claim 1, wherein the at least one *Bacillus* strain comprises the *Bacillus* strain having deposit accession number DSM 29869.

4. The animal feed or the animal feed additive according to claim 1, wherein the at least one *Bacillus* strain comprises the *Bacillus* strain having deposit accession number DSM 29871.

5. The animal feed or the animal feed additive according to claim 1, wherein the at least one *Bacillus* strain comprises the *Bacillus* strain having deposit accession number DSM 29872.

6. The animal feed or the animal feed additive according to claim 1, which further comprises a carrier.

7. The animal feed or the animal feed additive according to claim 6, wherein the carrier comprises one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch and cellulose.

8. The animal feed according to claim 1, wherein the bacterial count of each of said at least one *Bacillus* strain is between $1\times10^4$ and $1\times10^{14}$ CFU/kg of animal feed.

9. A method of improving one or more performance parameters of an animal selected from the group consisting of improving the feed conversion ratio, improving the body weight gain, improving the European Production Efficacy Factor, improving the feed efficiency and improving the health, said method comprising administering the animal feed or animal feed additive according to claim 1 to the animal.

10. The method according to claim 9, wherein the animal feed or the animal feed additive comprises the *Bacillus* strain having deposit accession number DSM 29870.

11. A method for feeding an animal comprising administering an animal feed or an animal feed premix comprising at least the *Bacillus* strain having deposit accession number DSM 29870 to said animal, optionally in conjunction with other animal feed ingredients.

12. The method according to claim 11, wherein the animal is selected from the group consisting of poultry and swine.

* * * * *